United States Patent [19]
Holton et al.

[11] Patent Number: 5,587,489
[45] Date of Patent: Dec. 24, 1996

[54] TAXANE AND BACCATIN III ANALOGS BEARING NEW C2 AND C4 FUNCTIONAL GROUPS

[75] Inventors: Robert A. Holton; Seokchan Kim, both of Tallahassee, Fla.

[73] Assignee: Florida State University, Tallahassee, Fla.

[21] Appl. No.: 372,103

[22] Filed: Jan. 13, 1995

Related U.S. Application Data

[62] Division of Ser. No. 10,798, Jan. 29, 1993, Pat. No. 5,399,726.

[51] Int. Cl.$^6$ .................. C07D 317/70; C07D 305/14
[52] U.S. Cl. .................. 549/229; 549/214; 549/228; 549/510; 549/511
[58] Field of Search .................. 549/510, 511, 549/214, 228, 229

[56] References Cited

U.S. PATENT DOCUMENTS

| | | | |
|---|---|---|---|
| 4,814,470 | 3/1989 | Colin et al. | 514/449 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 5,175,315 | 12/1992 | Holton | 549/510 |
| 5,352,806 | 10/1994 | Gunawardana et al. | 549/510 |
| 5,416,225 | 5/1995 | Danishefsky et al. | 549/341 |
| 5,488,116 | 1/1996 | Danishefsky et al. | 549/214 |

OTHER PUBLICATIONS

Kingston et al. "Progress in the Chemistry of Organic Natural Products" Springer–Verlag, New York (1993) pp. 26, 68, 176, 181, 183, 185, 189.

Holton et al. "A Synthesis of Taxusin" Journal of American Chemical Society, vol. 110 (1988) pp. 6558–6560.

Samaranayake et al. "Modified Taxols. 5.1 Reaction of Taxol with Electrophilic Reagents and Preparation of a Rearranged Taxol Derivative with Tubulin Assembly Activity3". Journal of Organic Chemistry, vol. 56, (1991) pp. 5114–5119.

Denis et al. "A Highly Efficient, Practical Approach to Natural Taxol" Journal of American Chemical Society, vol. 110 (1988) pp. 5917–5919.

Farina et al. "The Chemistry of Taxanes: Unexpected Rearrangement of Baccatin III During Chemoselective Debenzoylation with $Bu_3SnOMe/LiCl$" Tetrahedron Letters, vol. 33, No. 28 (1992) pp. 3979–3982.

Chen et al. "Taxol Structure–Activity Relationships: Synthesis and Biological Evaluation of 2–Deoxytaxol" Tetrahedron Letters, vol. 34, No. 20 (1993) pp. 3205–3206.

Miller et al., "Antileukemic Alkaloids from Taxus Wallichiana Zucc." Journal of Organic Chemistry, vol. 46 (1981) pp. 1469–1474.

Klein "Synthesis of 9–Dihydrotaxol: A Novel Bioactive Taxane" Tetrahedron Letters, vol. 34, No. 13 (1993) pp. 2047–2050.

*Primary Examiner*—Ba K. Trinh
*Attorney, Agent, or Firm*—Senniger, Powers, Leavitt & Roedel

[57] ABSTRACT

Process for the preparation of a derivative or analog of baccatin III or 10-desacetyl baccatin III having a C2 substituent other than benzoate and/or a C4 substituent other than acetate in which the C2 benzoate substituent and/or the C4 acetate substituent of a derivative of baccatin III or 10-desacetyl baccatin III is/are selectively reduced to the corresponding hydroxy group(s) and converted to $R_7COO$— and/or $R_8COO$—, respectively, wherein $R_7$ and $R_8$ are independently H, $C_1$–$C_6$ alkyl, $C_2$–$C_2$ alkenyl, $C_2$–$C_6$ alkynyl, moncyclic aryl, or monocyclic heteroaryl.

34 Claims, No Drawings

TAXANE AND BACCATIN III ANALOGS BEARING NEW C2 AND C4 FUNCTIONAL GROUPS

This invention was made with Government support under NIH Grant #CA 55131 awarded by the National Institute of Health. The Government has certain rights in the Invention.

REFERENCE TO RELATED APPLICATIONS

This application is a divisional application of U.S. Ser. No. 08/010,798, filed Jan. 29, 1993, now U.S. Pat. No. 5,399,726.

BACKGROUND OF THE INVENTION

The present invention relates to a process for the preparation of baccatin III and 10-desacetylbaccatin III analogs having new C2 and/or C4 functional groups.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds used in the process of the present invention.

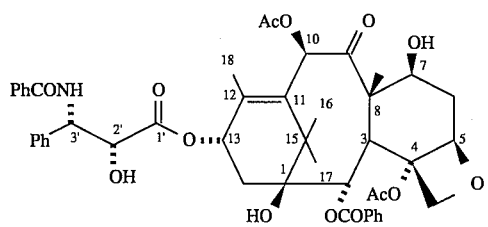

In Colin U.S. Pat. No. 4,814,470, it was reported that a taxol derivative, commonly referred to as taxotere, has an activity significantly greater than taxol. Taxotere has the following structure:

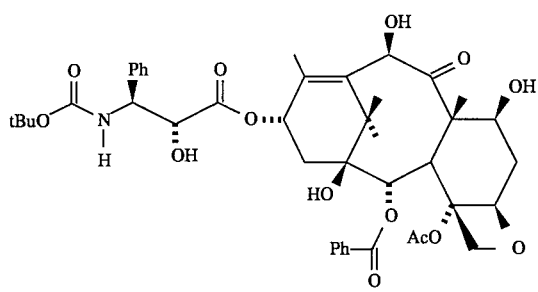

In copending application, U.S. Ser. No. 07/949,449, filed Sep. 22, 1992, it is reported that 10-desacetoxytaxol and related compounds also exhibit anti-tumor activity. Compounds disclosed in this copending application include:

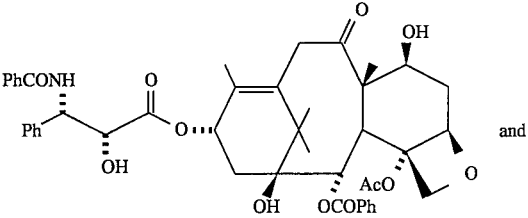

Taxol, taxotere and other biologically active tetracyclic taxanes may be prepared semisynthetically from baccatin III and 10-desacetyl baccatin III as set forth in U.S. Pat. Nos. 4,924,011 and 4,924,012 or by the reaction of a β-lactam and a suitably protected baccatin III or 10-desacetylbaccatin III ("10-DAB") derivative as set forth in U.S. Pat. No. 5,175,315 or copending U.S. patent application Ser. No. 07/949,107 (which is incorporated herein by reference). Baccatin III 1 and 10-DAB 2 can be separated from mixtures extracted from natural sources such as the needles, stems, bark or heartwood of numerous Taxus species and have the following structures.

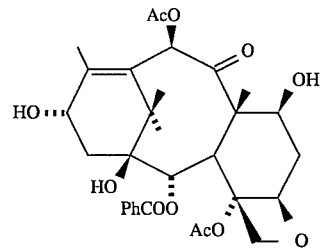

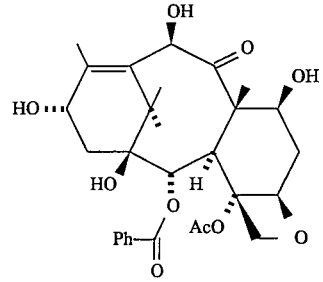

The tetracyclic core of taxol and taxotere bear six singly bonded oxygen substituents. Two of these (three in the case of taxotere) are present as hydroxyl groups, and the others are esters of three different carboxylic acids. Selective manipulation of these groups presents a formidable problem which must be overcome before a series of taxol analogs can be prepared by a rational synthetic sequence. Hydrolytic and solvolytic methods have previously encountered complications. For example, it has been reported by that hydrolysis of taxol under mildly basic conditions yields a complex mixture of products. Miller et al., *J. Org. Chem.* 1981, 46, 1469. Recently it has been found that solvolysis of baccatin (III) derivatives leads to rearrangement of the tetracyclic core. Farina, et al., Tetrahedron Lett. 1992, 33, 3979.

SUMMARY OF THE INVENTION

Among the objects of the present invention, therefore, is the provision of a process for selectively attaching different functional groups to the C2 and/or C4 oxygens of baccatin III and analogs or derivatives thereof; the provision of such a process which is relatively straightforward; the provision of such a process in which the C2 benzoate substituent of baccatin III and analogs or derivatives thereof may be selectively reduced and the provision of such a process in which the C4 acetate substituent may be selectively reduced.

Briefly, therefore, the present invention is directed to a process for the preparation of analogs or derivatives of baccatin III or 10-desacetyl baccatin III in which the C2 benzoate substituent and/or the C4 acetate substituent of baccatin III or 10-desacetoxy baccatin III are selectively reduced to the corresponding hydroxy group(s). The reduced baccatin III or 10-desacetyl baccatin III is thereafter converted to a baccatin III or 10-desacetyl derivative having the formula

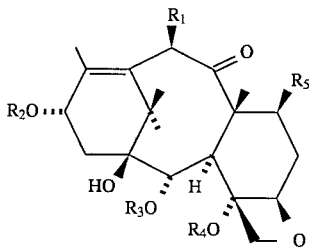

wherein $R_1$ is H, —OH, protected hydroxy, or —$OCOR_6$, $R_2$ is H, a hydroxy protecting group, or

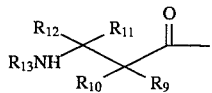

$R_3$ is H or $R_7CO$—, $R_4$ is H or $R_8CO$—, $R_5$ is H, —OH or protected hydroxy, $R_6$, $R_7$, and $R_8$ are independently H, $C_1$–$C_6$ alkyl, $C_2$–$C_6$ alkenyl, $C_2$–$C_6$ alkynyl, monocyclic aryl, or monocyclic heteroaryl.

$R_9$ is —$OR_{14}$, —$SR_{15}$, or —$NR_{16}R_{17}$;

$R_{10}$ is hydrogen, alkyl, alkenyl, alkynyl, aryl or heteroaryl;

$R_{11}$ and $R_{12}$ are independently hydrogen, alkyl, or alkenyl, alkynyl, aryl, acyl or heteroaryl, provided $R_{11}$ and $R_{12}$ are not both acyl;

$R_{13}$ is —$COR_{18}$, —$COOR_{18}$, —$COSR_{18}$, —$CONR_{12}R_{18}$, or —$SO_2R_{19}$, $R_{14}$ is hydrogen, alkyl, alkenyl, alkynyl, aryl, heteroaryl, or hydroxy protecting group, $R_{15}$ is alkyl, alkenyl, alkynyl, aryl, heteroaryl, or sulfhydryl protecting group, $R_{16}$ is hydrogen, alkyl, alkenyl, alkynyl, aryl, or heteroaryl;

$R_{17}$ is an amino protecting group;

$R_{18}$ is alkyl, alkenyl, alkynyl, aryl, or heteroaryl, and $R_{19}$ is alkyl, alkenyl, alkynyl, aryl, heteroaryl, —$OR_{15}$, or —$NR_{12}R_{16}$.

The present invention is additionally directed to a derivative of baccatin III or 10-desacetyl baccatin III having the formula

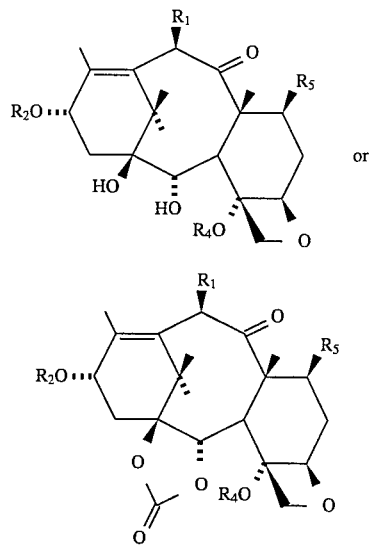

wherein $R_1$, $R_2$, R4, and $R_5$ are as previously defined.

Other objects and features of this invention will be in part apparent and in part pointed out hereinafter.

DETAILED DESCRIPTION OF THE INVENTION

As used herein "AR" means aryl; "Ph" means phenyl; "Ac" means acetyl; "R" means alkyl unless otherwise defined; "tBu" means t-butyl; "TES" means triethylsilyl; "TMS" means trimethylsilyl; "DMAP" means p-dimethylamino pyridine; "DMF" means dimethylformamide; "LDA" means lithium diisopropylamide; "LAH" means lithium aluminum hydride; "Red-Al" means sodium bis(2-methoxyethoxy) aluminum hydride; "10-DAB" means 10-desacetylbaccatin III; protected hydroxy means —OR wherein R is a hydroxy protecting group; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, dio, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The alkenyl groups described herein, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The alkynyl groups described herein, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, amido, etc.

Surprisingly, it has been discovered that the C2 ester of a suitably protected derivative of baccatin III or 10-DAB may be selectively reduced to form a 1,2 diol having the formula

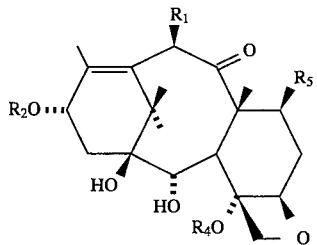

which may be converted to a 1,2 carbonate intermediate having the formula

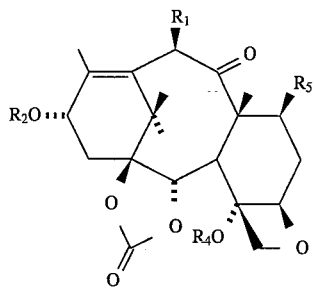

wherein $R_1$, $R_2$, $R_4$, and $R_5$ are as previously defined. This carbonate permits the selective formation of a variety of C2 esters through reaction with alkyl, alkenyl, alkynyl or aryl lithium reagents or Grignard reagents.

Any reducing agent which selectively reduces the C2 and/or C4 esters to the corresponding alcohol may be used. The reducing agent is preferably an aluminate and, most preferably, the reducing agent is lithium aluminum hydride ("LAH") or sodium bis(2-methoxyethoxy) aluminum hydride ("Red-Al").

After the C2 and/or C4 esters are reduced to the corresponding alcohol(s), standard acylating agents such as anhydrides and acid chlorides in combination with an amine such as pyridine, triethylamine, DMAP, or diisopropyl ethyl amine can be used to form new esters at C2 and/or C4. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

As will be discussed in greater detail below, baccatin III and 10-DAB derivatives having new C2 and/or C4 esters can be produced by several reaction schemes. To simplify the description, 10-DAB is used as the starting material in Reaction Schemes 1–6. It should be understood, however, that baccatin III derivatives or analogs may be produced using the same reactions (except for the protection of the C10 hydroxy group with TES) by simply replacing 10-DAB with baccatin III as the starting material.

10-DAB derivatives having a C2 hydroxy substituent or alternative C2 ester can be prepared as set forth in Reaction Scheme 1.

Scheme 1

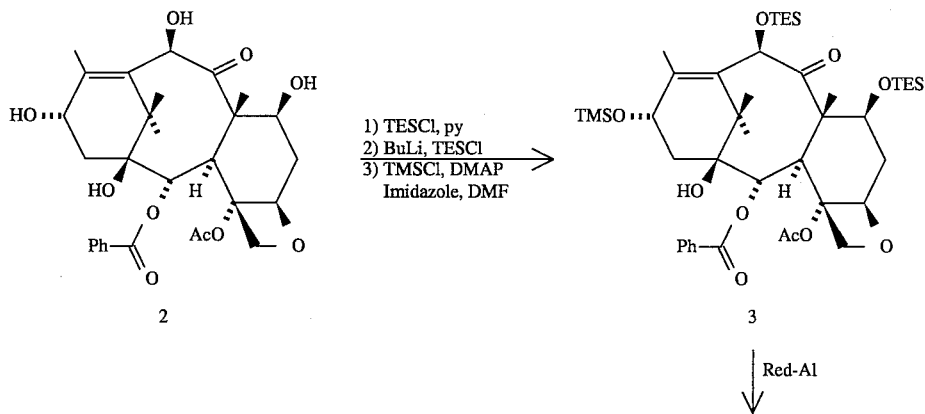

-continued
Scheme 1

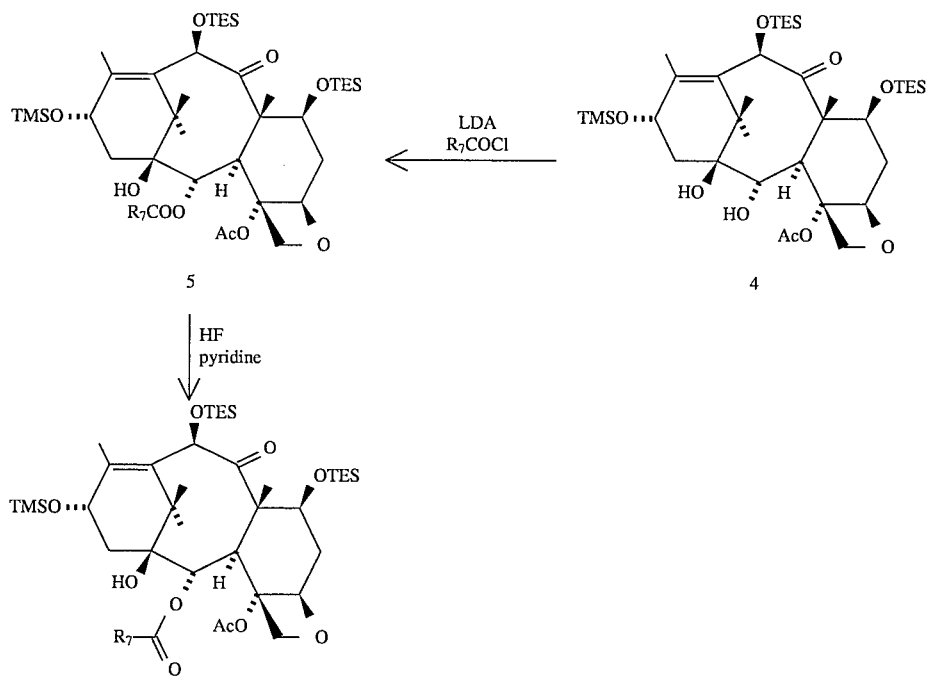

In Reaction Scheme 1, the C7 hydroxyl group of 10-deacetyl baccatin (III) was selectively protected as its triethylsilyl (TES) ether as described by Green, et al., JACS 110, 5917 (1988). The C10 hydroxyl group was then protected as the TES ether through the use of n-butyllithium and triethylsilyl chloride. The C13 hydroxyl group was subsequently protected as the trimethylsilyl (TMS) ether, which could be selectively removed at a later stage. The fully protected 13-O-trimethylsilyl-7,10-bis-O-triethylsilyll 10-deacetyl baccatin (III) 3 underwent selective reduction with Red-Al to give the 2 hydroxy derivative 4. Deprotonation of 4 with either n-butyllithium or a bulky amide base such as LDA was followed by the addition of an appropriate acid chloride to provide the C2 ester derivative 5. The C13 TMS group may then be removed using HF.

Alternatively, as shown in Reaction Scheme 2, 1,2 diol 4 can be readily converted to the 1,2 carbonate 6 which can be transformed to the C2 formate 5 ($R_3$=HCO) by treatment with Red-Al under mild conditions. In addition, carbonate 6 reacts selectively with nucleophilic agents (e.g., Grignard reagents or alkyllithium reagents) to provide the C2 ester derivative 5 ($R_3$=$R_7$CO). Again, the C13 TMS group may then be removed using HF.

Scheme 2

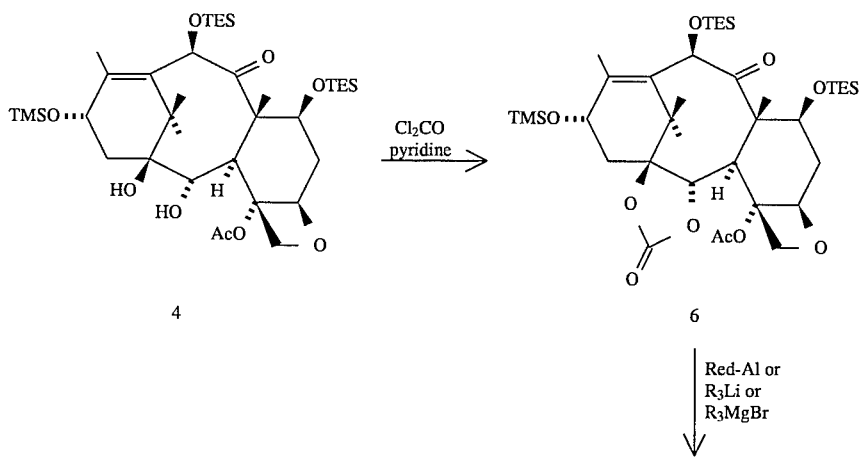

-continued
Scheme 2

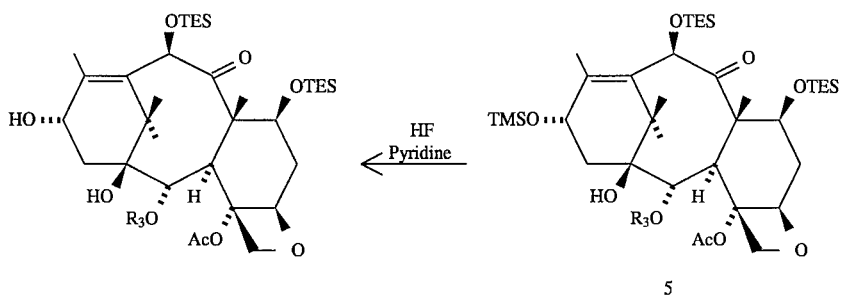

5

10-DAB analogs having different substituents only at C4, or at both C2 and C4 can be prepared as set forth in Reaction Schemes 3–6.

In Reaction Scheme 3, protected 1 0-DAB 3 is converted to the triol 7 with lithium aluminum hydride. Triol 7 is then converted to the corresponding C4 ester using $Cl_2CO$ in pyridine followed by a nucleophilic agent (e.g., Grignard reagents or alkyllithium reagents).

Scheme 3

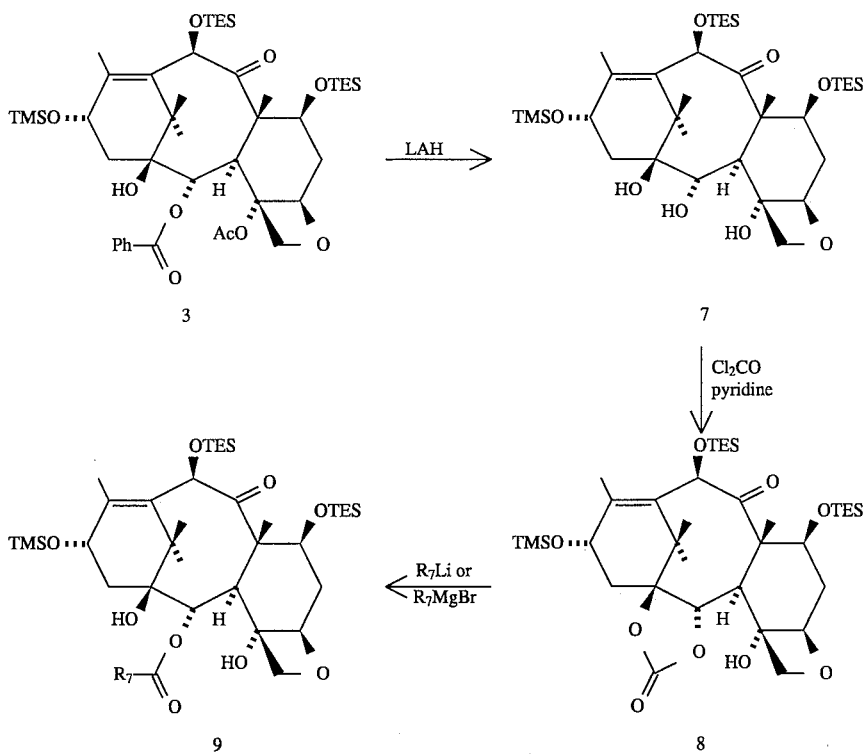

Alternatively, deprotonation of triol 7 with LDA followed by introduction of an acid chloride selectively gives the C4 ester. For example, when acetyl chloride was used, triol 7 was converted to 1,2 diol 4 as set forth in Reaction Scheme 4.

Scheme 4

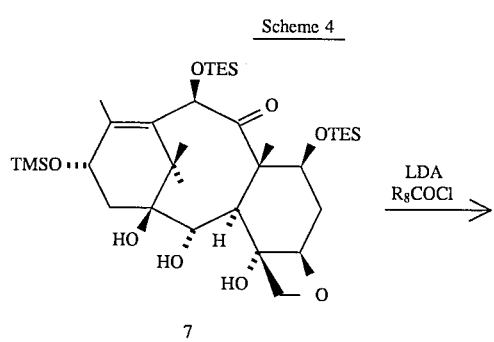

11

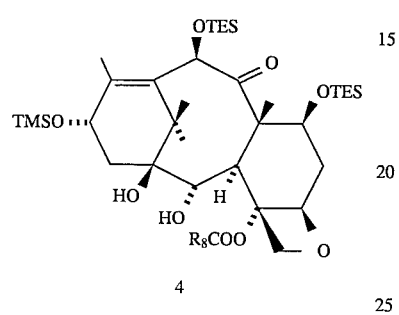

12

Triol 7 can also readily be converted to the 1,2 carbonate 8. Acetylation of carbonate 8 under vigorous standard conditions provides carbonate 6 as described in Reaction Scheme 5; addition of alkyllithiums or Grignard reagents to carbonate 6 provides the C2 ester having a free hydroxyl group at C4 as set forth in Reaction Scheme 2. As set forth in Reaction Scheme 6, other C4 substituents can be provided by reacting carbonate 8 with an acid chloride and a tertiary amine to yield carbonate 10 which is then reacted with alkyllithiums or Grignard reagents to provide 10-DAB derivatives having new substituents at C2 as set forth in Reaction Scheme 6.

Scheme 5

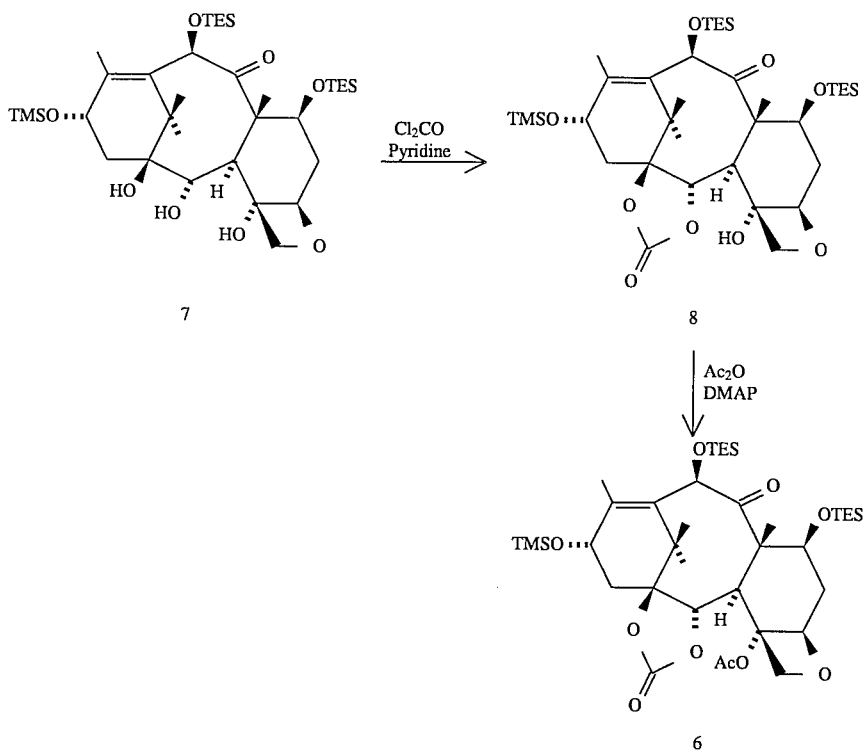

Scheme 6

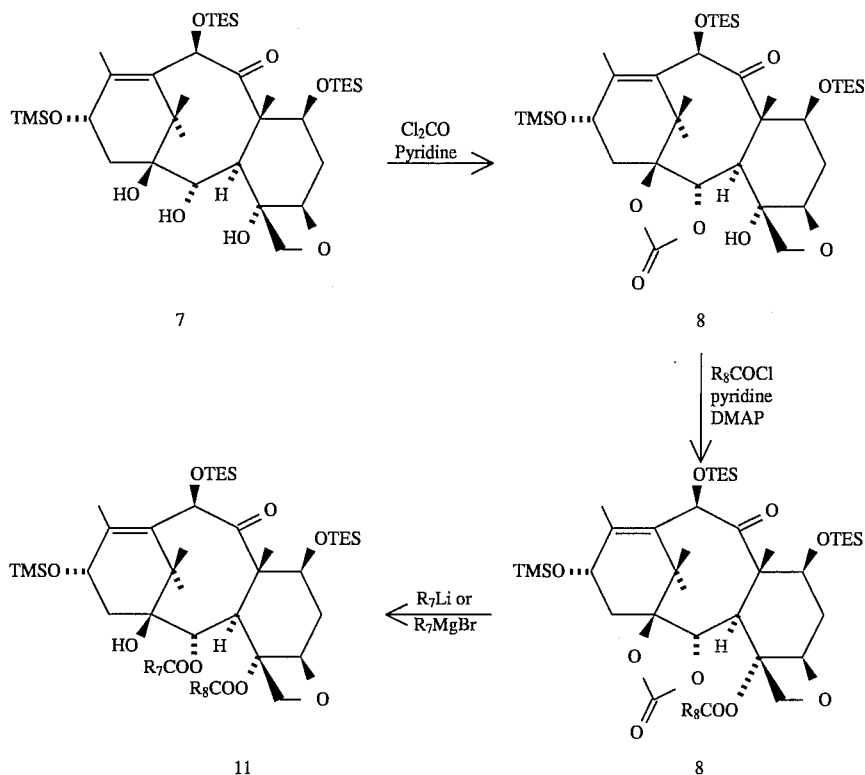

Alternatively, baccatin III may be used as a starting material and reacted as shown in Reaction Scheme 7. After being protected at C7 and C13, baccatin III is reduced with LAH to produce 1,2,4,10 tetraol 12. Tetraol 12 is converted to carbonate 13 using Cl₂CO and pyridine, and carbonate 13 is acylated at C10 with an acid chloride and pyridine to produce carbonate 14 (as shown) or with acetic anhydride and pyridine (not shown). Acetylation of carbonate 14 under vigorous standard conditions provides carbonate 15 which is then reacted with alkyl lithiums to provide the baccatin III derivatives having new substituents at C2 and C 10.

Scheme 7

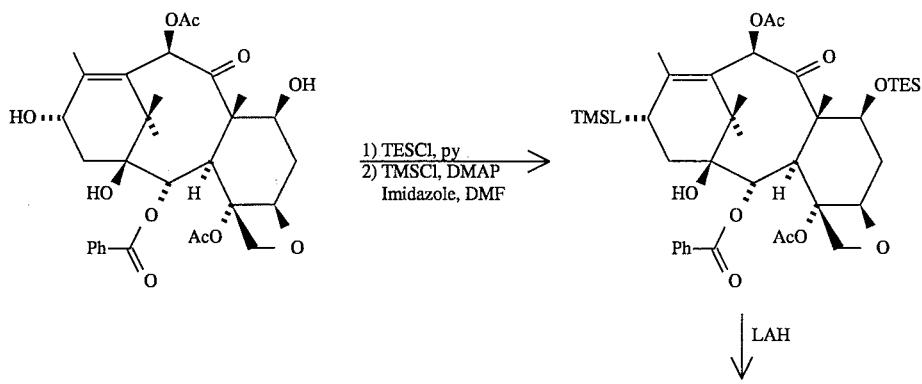

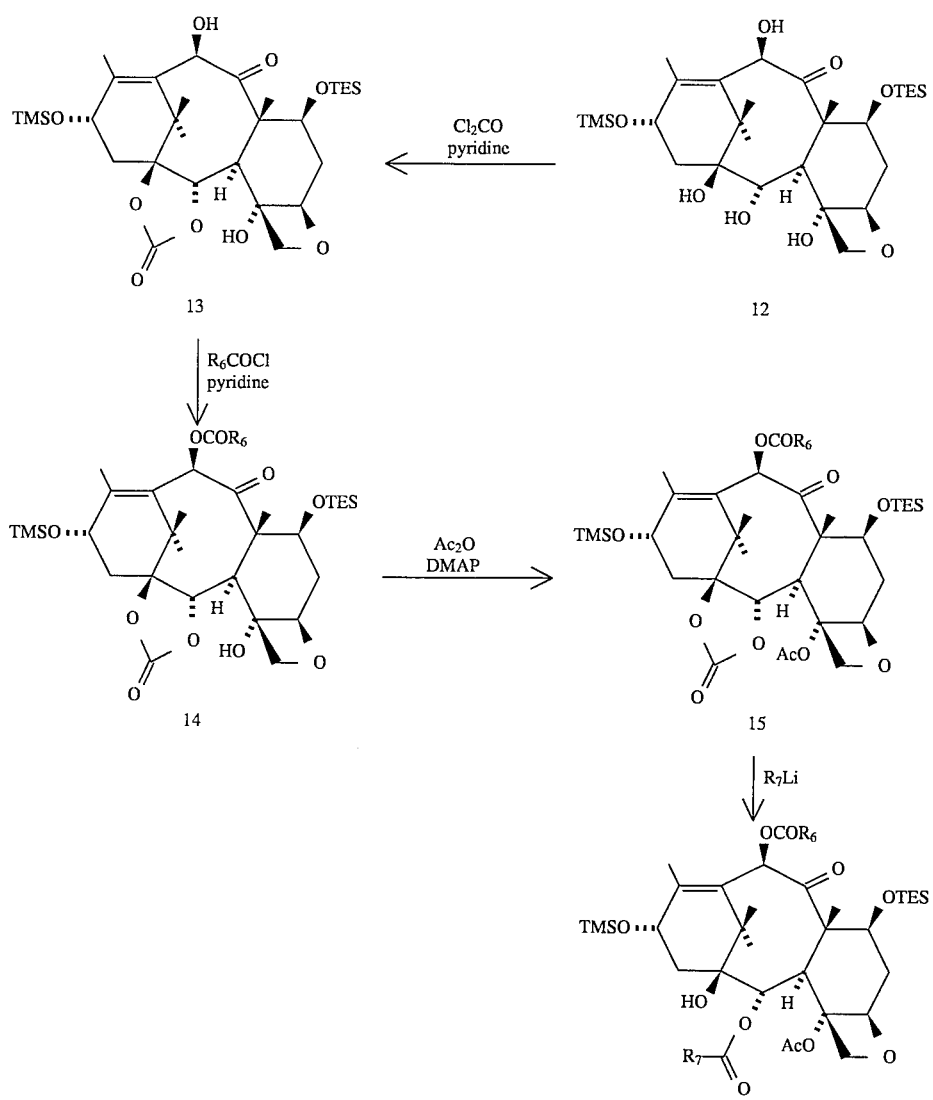

10-desacetoxy derivatives of baccatin III and 10-desoxy derivatives of 10-DAB having alternative C2 and C4 substituents may be produced using the same reactions (except for the protection of the C10 hydroxy group with TES) by simply replacing 10-DAB with 10-desacetoxy baccatin III as the starting material in Reaction Schemes 1–6. Baccatin III and 10-DAB may be selectively and nearly quantitatively converted to the corresponding 10-desacetoxy or 10-desoxytaxane when they are reacted with samarium diiodide. Alternatively, the 10-DAB derivatives having alternative C2 and C4 substituents may themselves be reacted with samarium diiodide to yield the corresponding 10-deacetoxy compound.

Synthesis of tetracyclic taxanes having a C13 side-chain and different substituents at C2 and/or C4 can readily be prepared from baccatin III and 10-DAB derivatives having different substituents at C2 and/or C4 using presently known methods. For instance, a suitable side chain may be attached to a baccatin III or 10-DAB derivative as set forth in U.S. Pat. Nos. 4,924,011 and 4,924,012 or by the reaction of a β-lactam and a suitably protected baccatin III or 10-desacetylbaccatin III derivative as set forth in U.S. Pat. No. 5,175,315 or copending U.S. patent application Ser. No. 07/949,107.

The following examples are provided to more fully illustrate the invention.

EXAMPLE 1

PROTECTION OF 10-DEACETYL BACCATIN (III) AT C7, C10, AND C13

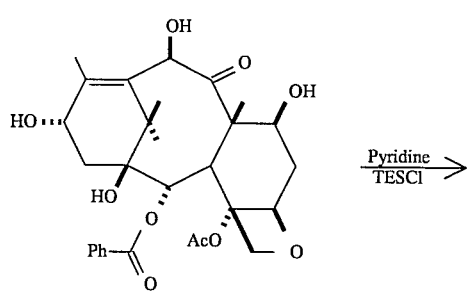

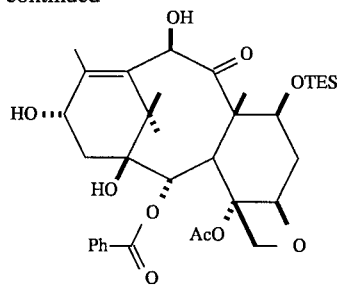

7-O-Triethylsilyl-10-deacetyl baccatin (III).

To a solution of 10-deacetyl baccatin (III) (1.5 g, 2.8 mmol) in 100 mL of pyridine was added 4.7 mL (10 eq) of triethylsilyl chloride (TESCl) and the mixture was stirred for 24 h at 25° C. The reaction mixture was diluted with EtOAc (800 mL) and washed with $H_2O$ (2×200 mL) and 10% aqueous $CuSO_4$ until all pyridine was removed. The organic layer was washed with brine (50.0 mL), dried over anhydrous $Na_2SO_4$, filtered, and concentrated to give crude product (1.92 g). Plug filtration from 20% EtOAc in hexane to 50% EtOAc in hexane gave 7-O-triethylsilyl-10-deacetyl baccatin (III) (1.78 g, 97.7%). m.p. 257°–258° C., $[\alpha]^{25}_{Na}$ −23.8° (c 0.5, $CHCl_3$), $^1H$ NMR ($CDCl_3$, 300 MHz), δ8.10 (d, J=7.1 Hz, 2H, benzoate ortho), 7.63–7.45 (m, 3H, aromatic), 5.60 (d, J=7.2 Hz, 1H, H2), 5.17 (d, J=1.7 Hz, 1H, H10), 4.95 (dd, J=1.7, 9.9 Hz, 1H, H5), 4.88 (m, 1H, H13), 4.41 (dd, J=6.6, 10.4 Hz, 1H, H7), 4.31 (d, J=8.2 Hz, 1H, H20α), 4.16 (d, J=8.2 Hz, 1H, H20β), 3.95 (d, J=7.1 Hz, 1H, H3), 2.49 (m, 1H, H6α), 2.28 (s, 3H, 4Ac), 2.10–2.09 (m, 2H, H14α, H14β), 2.08 (s, 3H, Me18), 1.90 (m, 1H, H6β), 1.73 (s, 3H, Me19), 1.19 (s, 3H, Me17), 1.08 (s, 3H, Me16), 1.02–0.93 (m, 9H, $SiCH_2C\underline{H}_3$), 0.5–0.51 (m, 6H, $SiC\underline{H}_2CH_3$).

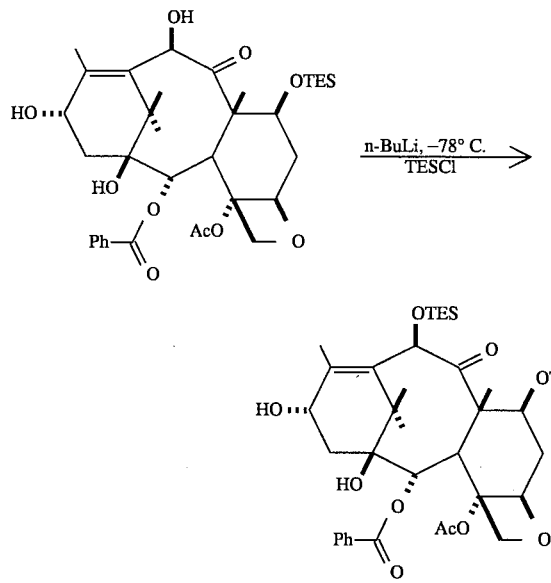

7,10-Bis-O-triethylsilyl-10-deacetyl baccatin (III).

To a solution of 7-O-triethylsilyl-10-deacetyl baccatin (III) (1.0 g, 1.55 mmol) in 20 mL of THF at −78° C. under $N_2$ was added 1.04 mL of a 1.64M solution of n-butyllithium (1.1 equiv) in hexane. The mixture was stirred for 30 rain at −78° C. and 0.31 mL (1.2 equiv) of TESCl was added dropwise. The mixture was stirred for 1 h at −78° C. and 10 mL of saturated aqueous $NaHCO_3$ was added. The solution was diluted with EtOAc (80.0 mL). The organic phase was washed with brine (15.0 mL), dried over anhydrous $Na_2SO_4$, filtered and concentrated under reduced pressure to give a crude solid (1.45 g). Flash chromatography from 25% EtOAc in hexane to 50% EtOAc in hexane gave 7,10-bis-O-triethylsilyl-10-deacetyl baccatin (III) (0.63 g, 53.6%) and recovered 7-O-triethylsilyl-10-deacetyl baccatin (III) (0.35 g, 35.0%). m.p. 184°–186° C., $[\alpha]^{25}_{Na}$ −46.0° (c 0.5, $CHCl_3$), $^1H$ NMR ($CDCl_3$, 300 MHz) δ8.10 (d, J=6.6 Hz, 2H, benzoate ortho), 7.6–7.4 (m, 3H, aromatic), 5.61 (d, J=7.1 Hz, 1H, H2), 5.21 (s, 1H, H10), 4.93 (dd, J=1.7, 9.3 Hz, 1H, H5), 4.82 (m, 1H, H13), 4.42 (dd, J=6.6, 10.4 Hz, 1H, H7), 4.27 (d, J=8.2 Hz, 1H, H20α), 4.14 (d, J=8.2 Hz, 1H, H20β), 3.91 (d, J=6.6 Hz, 1H, H3), 2.53 (m, 1H, H6α), 2.27 (s, 3H, 4Ac), 2.25 (m, 2H, H14α, H14β), 2.03 (s, 3H, Me18), 1.85 (m, 1H, H6β), 1.64 (s, 3H, Me19), 1.18 (s, 3H, Me17), 1.04 (s, 3H, Me16), 1.02–0.85 (m, 18H, $SiCH_2C\underline{H}_3$), 0.69–0.58 (m, 12H, $SiC\underline{H}CH_3$).

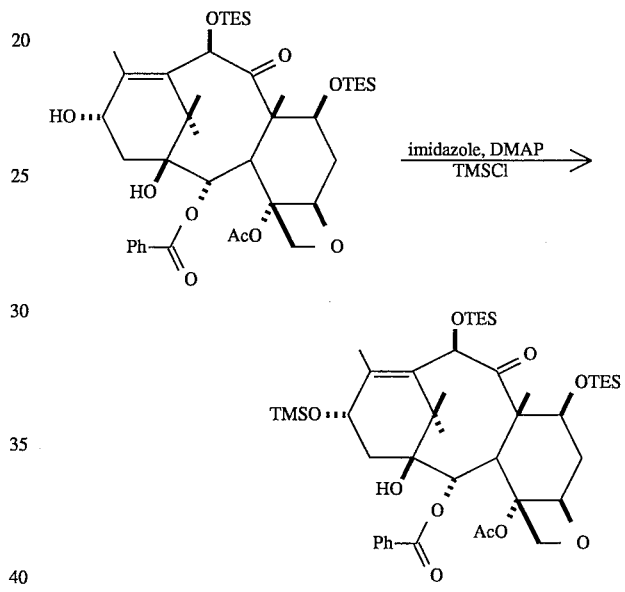

13-O-Trimethylsilyl-7,10-bis-O-triethylsilyl-10-deacetyl baccatin (III).

To a solution of 0.5 g (0.66 mmol) of 7,10-bis-O-triethylsilyl-10-deacetyl baccatin (III), 90 mg (2 eq) of imidazole, 40 mg (0.5 eq) of p-dimethylaminopyridine (DMAP) in 15 mL of $CH_2Cl_2$ at 0° C. was added 0.17 mL (2 eq) of trimethylsilyl chloride (TMSCl). The solution was stirred at 0° C. for 30 min and 1.0 mL of methanol was added. The mixture was diluted with $H_2O$ (10.0 mL) and EtOAc (50.0 mL) and the organic layer was separated, washed with brine (10.0 mL), dried over anhydrous $Na_2SO_4$, filtered and concentrated under reduced pressure to afford a crude solid (0.58 g). Plug filtration with 10% EtOAc in hexane gave 13-O-trimethylsilyl-7,10-bis-O-triethylsilyl-10-deacetyl baccatin (III) (0.53 g, 96.5%). m.p. 213°–215° C., $[\alpha]^{25}_{Na}$ −43.0° (c 0.5, $CHCl_3$), $^1H$ NMR ($CDCl_3$, 300 MHz), δ8.10 (d, J=7.1 Hz, 2H, benzoate ortho), 7.6–7.4 (m, 3H, aromatic), 5.62 (d, J=7.1 Hz, 1H, H2), 5.19 (s, 1H, H10), 4.94 (dd, J=1.8, 8.8 Hz, 1H, H5), 4.86 (m, 1H, H13), 4.41 (dd, J=6.6, 10.4 Hz, 1H, H7), 4.28 (d, J=8.2 Hz, 1H, H20α), 4.12 (d, J=8.2 Hz, 1H, H20β), 3.86 (d, J=7.14 Hz, 1H, H3), 2.51 (m, 1H, H6α), 2.26 (s, 3H, 4Ac), 2.22–2.03 (m, 2H, H14α, H14β), 1.93 (s, 3H, Me18), 1.84 (m, 1H, H6β), 1.64 (s, 3H, Me19), 1.19 (s, 3H, Me17), 1.12 (s, 3H, Me16), 1.02–0.93 (m, 18H, $SiCH_2C\underline{H}_3$), 0.69–0.56 (m, 12H, $SiC\underline{H}_2CH_3$), 0.17 (s, 9H, $SiC\underline{H}_3$).

EXAMPLE 2

PREPARATION OF TAXOL ANALOGS WITH VARIOUS SUBSTITUENTS AT C-2 a. 13-O-Trimethylsilyl-7,10-bis-O-triethylsilyl-2-debenzoyl-2-acetyl-10-deacetyl baccatin (III).

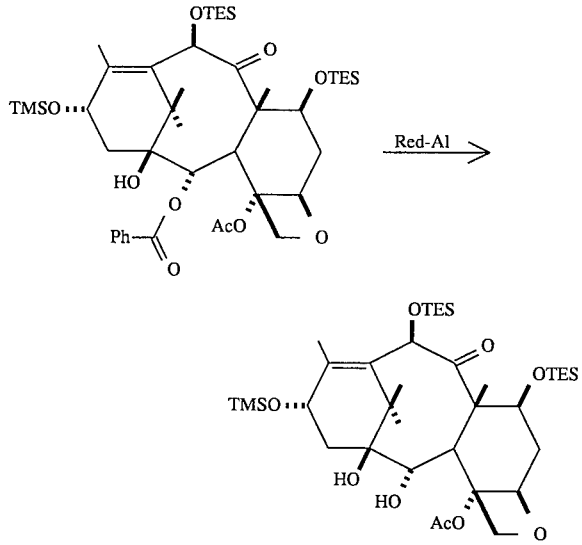

13-O-Trimethylsilyl-7,10-bis-O-triethylsilyl-2-debenzoyl-10,deacetyl baccatin (III).

To a solution of 13-O-trimethylsilyl-7,10-bis-O-triethylsilyl10-deacetyl baccatin (III) (0.1 g, 0.12 mmol) in THF (6.0 mL) at 0° C. was added dropwise 60 µL of a 1.0M solution of Red-Al in toluene. The resulting mixture was stirred at 0° C. for 1 h and 3.0 mL of saturated aqueous NaHCO₃ was added. The solution was filtered and the solid was rinsed with EtOAc. The filtrate was concentrated under reduced pressure and diluted with EtOAc (50.0 mL). The organic layer was separated and washed with brine (5.0 mL). The combined organic layer was dried over anhydrous Na$_2$SO$_4$, filtered, and concentrated under reduced pressure to give a crude solid (0.14 g). Flash chromatography with 30% EtOAc in hexane gave pure 13-O-trimethylsilyl-7,10-bis-O-triethylsilyl-2-debenzoyl-10-deacetyl baccatin (III) (84.5 mg, 96.6%). m.p. 73°–74° C., $[\alpha]^{25}_{Na}$ −24.0° (c 0.5, CHCl$_3$), $^1$H NMR (CDCl$_3$, 300 MHz), δ5.11 (s, 1H, H10), 4.94 (dd, J=1.7, 9.3 Hz, 1H, H5), 4.87 (m, 1H, H13), 4.62 (d, J=9.3 Hz, 1H, H20α), 4.54 (d, J=8.8 Hz, 1H, H20α), 4.35 (dd, J=6.6, 10.4 Hz, 1H, H7), 3.86 (m, 1H, H2), 3.47 (d, J=6.6 Hz, 1H, H3), 2.51 (m, 1H, H6α,), 2.14 (s, 3H, 4Ac), 2.02–1.83 (m, 3H, H14α, H14β, H6β), 1.60 (s, 3H, Me18), 1.60 (s, 3H, Me19), 1.14 (s, 3H, Me17), 1.07 (s, 3H, Me16), 0.99–0.92 (m, 18H, SiCH$_2$CH$_3$), 0.66–0.55 (m, 12H, SiCHCH$_3$),0.13 (s, 9H, SiCH$_3$).

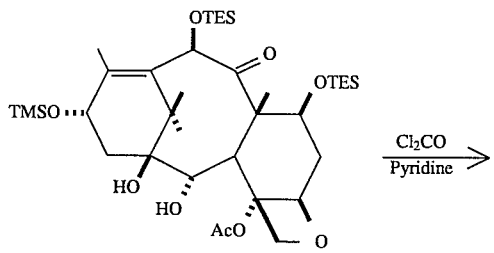

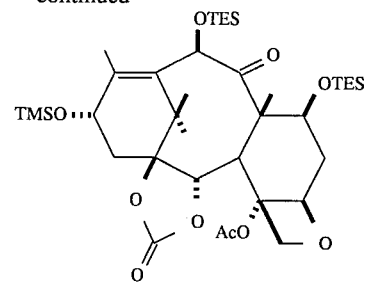

13-O-Trimethylsilyl-7,10-bis-O-triethylsilyl-2-debenzoyl-10-deacetyl baccatin (III) 1,2-carbonate.

To a solution of 13-O-trimethylsilyl-7,10-bis-O-triethylsilyl-2-debenzoyl-10-deacetyl baccatin (III) (20.0 mg, 0.027 mmol) in CH$_2$Cl$_2$(4.0 mL) and pyridine (0.8 mL) at −78° C. was added 80 µL of a 3.4M solution of COCl$_2$ in benzene (10 eq). The mixture was warmed to −10° C. (ice-acetone) and kept for 30 min at −10° C. Saturated aqueous NaHCO$_3$ (5.0 mL) was added and the mixture were extracted with EtOAc (3×10 mL). The organic layer was washed with aqueous 10% CuSO$_4$ until all pyridine disappeared then brine (5.0 mL). The combined organic layer was dried over anhydrous Na$_2$SO$_4$, filtered and concentrated under reduced pressure to give a crude solid (22.5 mg). Plug filtration with 20% EtOAc in hexane gave pure 13-O-trimethylsilyl-7,10-bis-O-triethylsilyl- 2-debenzoyl-10-deacetyl baccatin (III) 1,2-carbonate (20.5 mg, 99.0%). m.p. 144°–146° C., $[\alpha]^{25}_{Na}$ −27.5° (c 0.5, CHCl$_3$), $^1$H NMR (CDCl$_3$, 300 MHz), δ5.15 (s, 1H, H10), 4.90 (m, 2H, H5, H13), 4.58 (d, J=8.9 Hz, 1H, H20α), 4.44 (d, J=8.6 Hz, 1H, H20β), 4.43 (d, J=5.4 Hz, 1H, H2), 4.37 (dd, J=6.6, 10.4 Hz, 1H, H7), 3.43 (d, J=5.6 Hz, 1H, H3), 2.56 (m, 1H, H6α), 2.37 (m, 1H, 14α), 2.14 (s, 3H, 4Ac), 2.13 (m, 1H, H14β), 1.92 (s, 3H, Me18), 1.84 (m, 1H, H6β), 1.64 (s, 3H, Me19), 1.22 (s, 3H, Me17), 1.17 (s, 3H, Me16), 0.99–0.85 (m, 18H, SiCH$_2$CH$_3$), 0.66–0.55 (m, 12H, SiCHCH$_3$), 0.17 (s, 9H, SiCH$_3$).

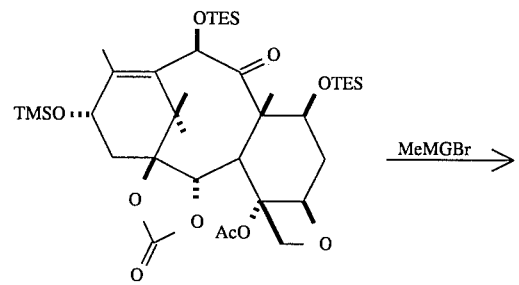

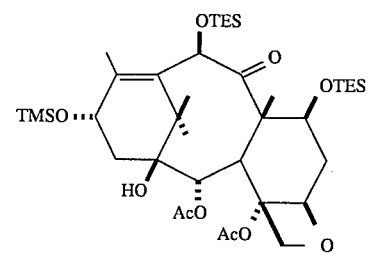

13-O-Trimethylsilyl -7,10-bis-O-triethylsilyl-2-debenzoyl-2-acetyl-10-deacetyl baccatin (III). To a solution of 13-O-trimethylsilyl-7,10-bis-O-triethylsilyl-2-debenzoyl-10-deacetyl baccatin (III) 1,2-carbonate (10.0 mg, 0.014 mmol) in THF (0.5 mL) at 0° C. was added 40 µL of a 3.4M solution (10 eq) of MeMgBr in ether. The solution was stirred for 1 h at 0° C. under N$_2$ and saturated aqueous NaHCO$_3$ was added (1.0 mL). The mixture was extracted with EtOAc (3×5.0 mL) and the organic layer was washed with brine (5.0 mL), dried over anhydrous Na₂SO₄, filtered and concentrated under reduced pressure to give a crude solid (11.3 mg). Flash chromatography with 20% EtOAc in hexane gave pure 13-O-trimethylsilyl-7,10-bis-O-triethylsilyl-2-debenzoyl-2acetyl-10-aleacetyl baccatin (III) (9.8 mg, 95.9%). m.p. 201°–203° C., $[\alpha]^{25}_{Na}$ –38.9° (c 0.5, CHCl₃), ¹H NMR (CDCl₃, 300 MHz), δδ 5.34 (d, J=7.2 Hz, 1H, H2), 5.15 (s, 1H, H10), 4.93 (dd, J=2.8, 9.3 Hz, 1H, H5), 4.83 (m, 1H, H13), 4.43 (d, J=7.7 Hz, 1H, H20α), 4.38 (d, J=7.1 Hz, 1H, H20β), 4.18 (dd, J=6.1, 11.6 Hz, 1H, H7), 3.73 (d, J=6.6 Hz, 1H, H3), 2.54 (m, 1H, H6α, 2.20–2.03 (m, 2H, H14α, H14β), 2.15 (s, 3H, 4Ac), 2.07 (s, 3H, 2Ac), 1.96 (m, 1H, H6β), 1.89 (s, 3H, Me18), 1.58 (s, 3H, Me19), 1.12 (s, 3H, Me17), 1.00 (s, 3H, Me16), 0.99–0.91 (m, 18H, SiCH₂C$\underline{H}$₃), 0.67–0.56 (m, 12H, SiC$\underline{H}$₂CH₃), 0.16 (s, 9H, SiC$\underline{H}$₃).

b. 13-O-Trimethylsilyl-7,10-bis-O-triethylsilyl-2-debenzoyl-10deacetyl baccatin (III)

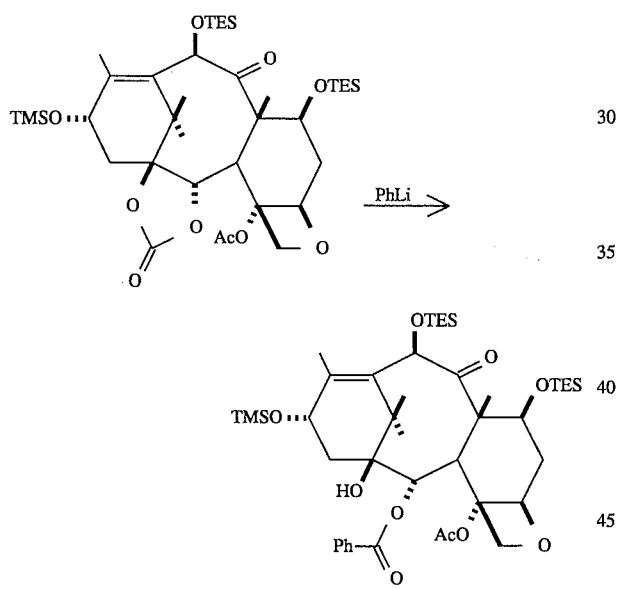

To a solution of 13-O-trimethylsilyl-7,10-bis-O-triethylsilyl-2-debenzoyl-10-deacetyl baccatin (III) 1,2-carbonate (10.0 mg, 0.014 mmol) in THF (0.5 mL) at –45° C. was added 78 μL of a 1.8M solution of phenyllithium (10 eq) in 30% ether/70% cyclohexane. The solution was stirred for 1 h at –45° C. under N2 and saturated aqueous NaHCO was added (1.0 mL). The mixture was extracted with EtOAc (3×5.0 mL). The organic layer was washed with brine (5.0 mL), dried over anhydrous Na₂SO₄, filtered and concentrated under reduced pressure to give a crude solid (12.5 mg). Flash chromatography with 10% EtOAc in hexane gave pure 13-O-trimethylsilyl-7,10-bis-O-triethylsilyl-2-debenzoyl-10-deacetyl baccatin (III) (10.8 mg, 94.5%). 13-O-Trimethylsilyl-7,10-bis-O-triethylsilyl-2-debenzoyl-10-deacetyl baccatin (III)

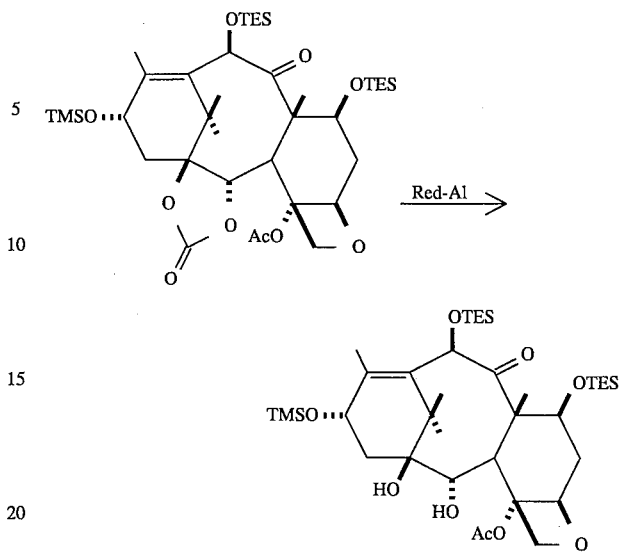

To a stirred solution of 13-O-trimethylsilyl-7,10-bis-O-triethylsilyl-2-debenzoyl-10-deacetyl baccatin (III) 1,2-carbonate (6.0 mg, 0.0082 mmol) in THF (0.5 mL) at 0° C. was added 60 μL of a 0.068M solution (5 eq) of Red-Al in toluene. The resulting solution was stirred for 1 h at 0° C. under N₂, 1.0 mL of saturated aqueous NaHCO₃ was added, and the mixture was extracted with EtOAc (2×10.0 mL). The organic layer was washed with brine (5.0 mL), dried over anhydrous Na₂SO₄, filtered and concentrated under reduced pressure to give a crude solid (6.75 mg). Flash chromatography with 30% EtOAc in hexane gave 13-O-trimethylsilyl-7,10-bis-O-triethylsilyl-2-debenzoyl-10-deacetyl baccatin (II) (4.3 mg, 71.5%) and 13-O-trimethylsilyl-7,10-bis-O-triethylsilyl-2-debenzoyl-2-formyl-10-deacetyl baccatin (III) (1.5 mg, 24.5%).

d. 13-O-Trimethyisilyl-7,10-bis-O-triethylsilyl-2-debenzoyl-2-p-fluorobenzoyl-10-deacetyl baccatin (III)

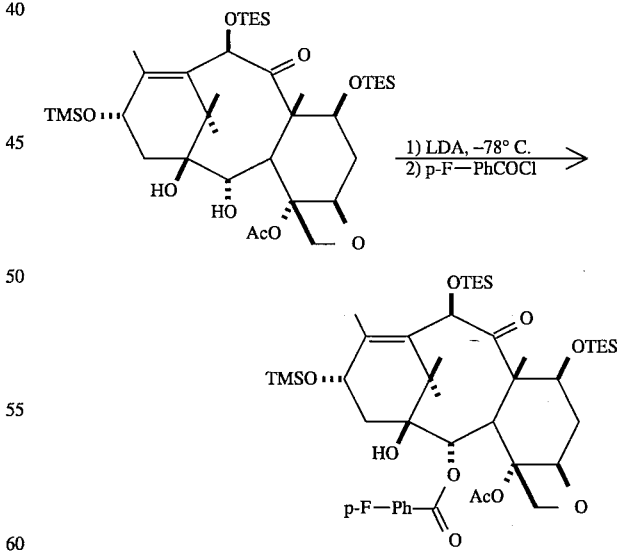

To a solution of 13-O-trimethylsilyl-7,10-bis-O-triethylsilyl-2-debenzoyl-10-deacetyl baccatin (III) (40.0 mg, 0.054 mmol) in THF (1.0 ml) at –78° C. under N₂ was added dropwise 320 μL of a 0.328M solution (2 eq) of LDA in THF. The mixture was stirred for 30 min at –78° C and a solution of 26 μL (4 eq) of p-fluorobenzoyl chloride in 100

μL of THF was added. After 1 h diisopropylamine (100 μL) was added and the mixture was warmed to 25° C. After 10 min the mixture was diluted with aqueous NaHCO$_3$ (5.0 mL) and extracted with EtOAc (2×10.0 mL). The organic layer was washed with brine (5.0 mL), dried over anhydrous Na$_2$SO$_4$, filtered and concentrated under reduced pressure to give a crude solid (67.5 mg). Flash chromatography with 10% EtOAc in hexane gave 13-O-trimethylsilyl-7,10-bis-O-triethylsilyl-2-debenzoyl-2-p-fluorobenzoyl-10-deacetyl baccatin (III) (36.9 mg, 80.2%). m.p. 216°–218° C., [α]$^{25}_{Na}$ −45.6° (c 0.5, CHCl$_3$), $^1$H NMR (CDCl$_3$, 300 MHz)δ8.10 (m, 2H, aromatic), 7.18–7.12 (m, 2H, aromatic), 5.60 (d, J=7.2 Hz, 1H, H2), 5.19 (s, 1H, H10), 4.94 (dd, J=1.7, 9.9 Hz, 1H, H5), 4.86 (m, 1H, H13), 4.41 (dd, J=6.9, 10.4 Hz, 1H, H7), 4.26 (d, J=8.2 Hz, 1H, H20α), 4.11 (d, J=8.2 Hz, 1H, H20α), 3.6 (d, J=6.6 Hz, 1H, H3), 2.51 (m, 1H, H6α), 2.25 (s, 3H, 4Ac), 2.11 (m, 2H, H14α, H14β), 2.04 (s, 3H, Me18), 1.88 (m, 1H, H6β), 1.64 (s, 3H, Me19), 1.18 (s, 3H, Me17), 1.12 (s, 3H, Me16), 1.02–0.92 (m, 18H, SiCH$_2$C$\underline{H}_3$), 0.69–0.54 (m, 12H, SiC$\underline{H}_2$CH$_3$), 0.17 (s, 9H, SiC$\underline{H}_3$).

7,10-Bis-O-triethylsilyl-2-debenzoyl-2-p-fluorobenzoyl-10-deacetyl baccatin (III)

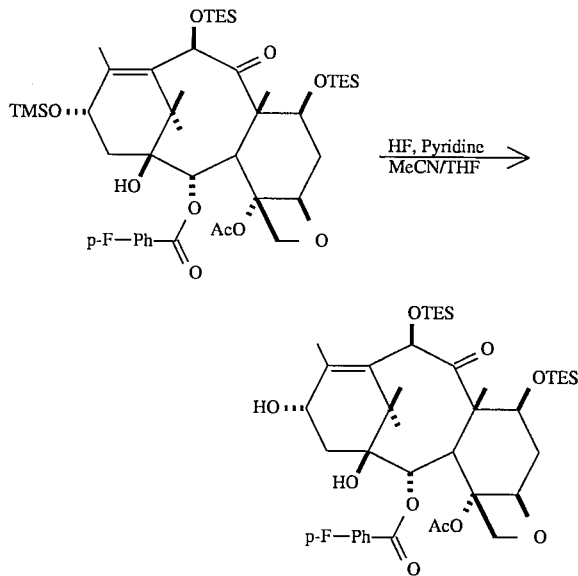

To a solution of 13-O-trimethylsilyl-7,10-bis-O-triethylsilyl-30.0 mg, 0.035 mmol) in 2.25 mL of acetonitrile and 2.25 mL of THF in a polyethylene vial was added dropwise 48 μL of pyridine and 75 μL of 48% aqueous HF. The reaction mixture was stirred at 25° C. for 12 h and then diluted with EtOAc (20.0 mL). Saturated aqueous NaHCO$_3$ was added until gas evolution ceased. The organic layer was separated, washed with brine (3.0 mL), dried over anhydrous Na$_2$SO$_4$, filtered and concentrated under reduced pressure to give a crude solid (36.2 mg). Flash chromatography with 25% EtOAc in hexane gave 7,10-bis-O-triethylsilyl-2-debenzoyl-2-p-fluorobenzoyl-10-deacetyl baccatin (III) (21.5 mg, 78.8%) and 10-O-triethylsilyl-2-debenzoyl-2-p-fluorobenzoyl-10-deacetyl baccatin (III) (3.8 mg, 15.9%). m.p. 186°–188° C., [α]$^{25}_{Na}$ 48.2° (c 0.5, CHCl$_3$), $^1$H NMR (CDCl$_3$, 300 MHz) δ8.11 (m, 2H, aromatic), 7.26–7.11 (m, 2H, aromatic), 5.59 (d, J=6.6 Hz, 1H, H2), 5.21 (s, 1H, H10), 4.94 (dd, J=1.7, 9.34 Hz, 1H, H5), 4.84 (m, 1H, H13), 4.42 (dd, J=6.6, 10.4 Hz, 1H, H7), 4.26 (d, J=8.24 Hz, 1H, H20α), 4.14 (d, J=8.25 Hz, 1H, H20β), 3.90 (d, J=6.6 Hz, 1H, H3), 2.54 (m, 1H, H6α), 2.26 (s, 3H, 4Ac), 2.05 (m, 2H, H14α, H14β), 2.02 (s, 3H, Me18), 1.88 (m, 1H, H6β), 1.65 (s, 3H, Me19), 1.18 (s, 3H, Me17), 1.05 (s, 3H, Me16), 1.02–0.92 (m, 18H, SiCH$_2$C$\underline{H}_3$), 0.69–0.53 (m, 12H, SiC$\underline{H}_2$CH$_3$).

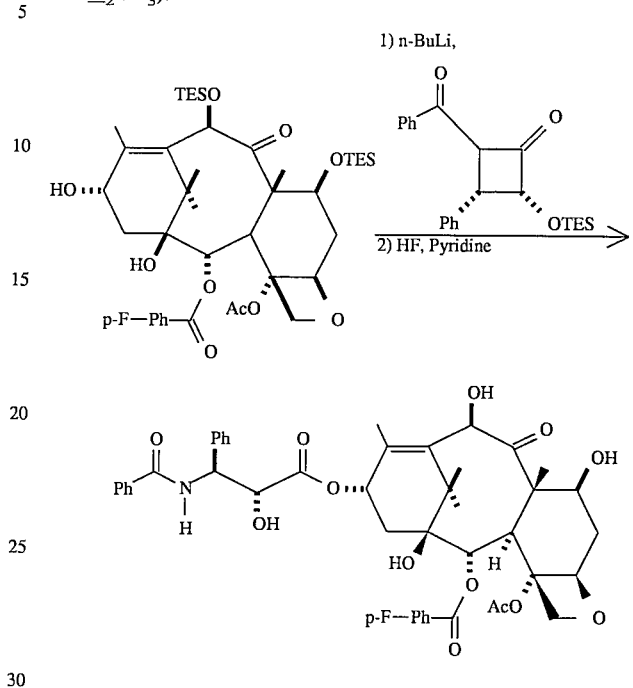

To a solution of 7,10-bis-O-triethylsilyl-2-debenzoyl-2-p-fluoro-benzoyl-10-deacetyl baccatin (III) (20.0 mg, 0.026 mmol) in 1.0 mL of THF at −45° C. was added dropwise 16 μL of a 1.64M solution of n-butyllithium in hexane. After 0.5 h at −45° C., a solution of (±) cis-1-benzoyl-3-triethylsilyloxy-4-phenyl azetidin-2-one (50.0 mg, 0.13 mmol) in THF (0.5 mL) was added dropwise to the mixture. The solution was warmed to 0° C. and kept at that temperature for 1 h and 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel with 20% EtOAc in hexane to give a crude solid (32.5 mg). To a solution of this solid in 1.6 mL of acetonitrile and 79 μL of pyridine at 0° C. was added 240 μL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave a crude solid (24.4 mg) which was purified by flash chromatography with 70% EtOAc in hexane to give 2-debenzoyl-2-p-fluorobenzoyl taxol (15.2 mg, 70.4%). m.p. 180°–183° C., −56.9° (c 0.5, CHCl$_3$), $^1$H NMR (CDCl$_3$ 300 MHz) δ8.15 (m, 2H, aromatic), 7.73 (m, 2H, aromatic), 7.52–7.34 (m, 8H, aromatic), 7.20 (m, 2H, aromatic), 7.07 (d, J=9.3 Hz, 1H, NH), 6.22 (dd, J=8.8, 8.8 Hz, 1H, H13), 5.79 (dd, J=8.8, 2.7 Hz, 1H, H3'), 5.64 (d, J=7.1 Hz, 1H, H2β), 5.17 (s, 1H, H10), 4.94 (dd, J=9.3, 1.7 Hz, 1H, H5), 4.79 (m, 1H, H2'), 4.29–4.15 (m, 3H, H7, H20α, H20β), 3.90 (d, J=7.1 Hz, 1H, H3), 3.56 (d, J=5.0 Hz, 1H, 2'OH), 2.58 (m, 1H, H6α), 2.38 (s, 3H, 4Ac), 2.28 (m, 2H, H14α, H14β), 1.82 (m, 1H, H6β), 1.79 (s, 3H, Me18), 1.74 (s, 3H, Me19), 1.20 1.20 (s, 3H, Me17), 1.10 (s, 3H, Me16).

g. 13-O-Trimethyisilyl-7,10-bis-O-triethylsilyl-2-debenzoyl-2-(2-furoyl)-10-deacetyl baccatin (III)

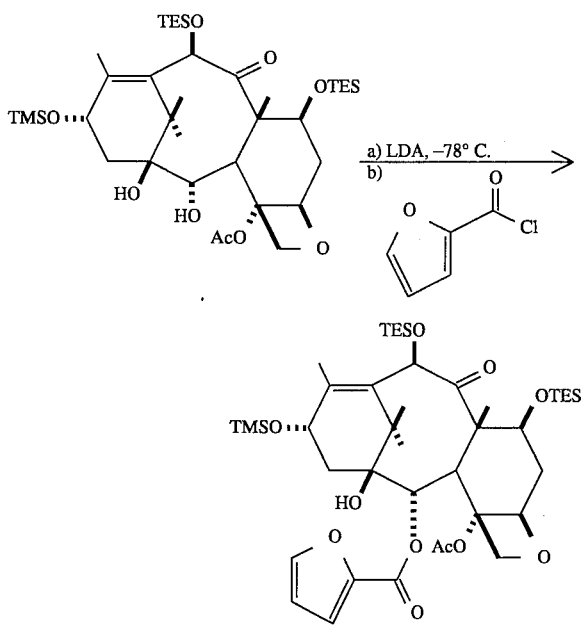

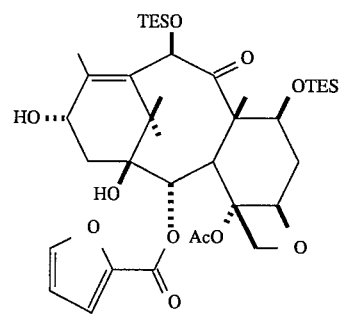

To a solution of 13-O-trimethylsilyl-7,10-bis-O-triethylsilyl-2-debenzoyl-10-deacetyl baccatin (III) (40.0 mg, 0.054 mmol) in THF (1.0 mL) at −78° C. under N₂ was added dropwise 320 μL of a 0.328M solution (2 eq) of LDA in THF. The mixture was stirred for 30 rain at −78° C. and a solution of 26 μL (4 eq) of p-fluorobenzoyl chloride in 100 μL of THF was added. After 1 h diisopropylamine (100 μL) was added and the mixture was warmed to 25° C. After 10 min the mixture was diluted with aqueous NaHCO₃ (5.0 mL) and extracted with EtOAc (2×10.0 mL). The organic layer was washed with brine (5.0 mL), dried over anhydrous Na₂SO₄, filtered and concentrated under reduced pressure to give a crude solid (64.2 mg). Flash chromatography with 15% EtOAc in hexane gave 13-O-trimethylsilyl-7,10-bis-O-triethylsilyl-2-debenzoyl-2-(2-furoyl)-10-deacetyl baccatin (III) (33.9 mg, 76.3%). m.p. 208°–210° C., $[\alpha]^{25}_{Na}$ −49.6° (c 0.5, CHCl₃), ¹H NMR (CDCl₃, 300 MHz) δ7.62 (m, 1H, furoyl), 7.20 (m, 1H, furoyl), 6.50 (m, 1H, furoyl), 5.52 (d, J=7.1 Hz, 1H, H2), 5.18 (s, 1H, H10), 4.95 (dd, J=1.6, 9.4 Hz, 1H, H5), 4.85 (m, 1H, H13), 4.41 (dd, J=6.9 10.4 Hz, 1H, H7), 4.38 (d, J=8.8 Hz, 1H, H20α), 4.15 (d, J=8.2 Hz, 1H, H20β), 3.82 (d, J=6.6 Hz, 1H, H3), 2.51 (m, 1H, H6α), 2.22 (s, 3H, 4Ac), 2.10 (m, 2H, H14α, H14β), 1.92 (s, 3H, Me18), 1.89 (m, 1H, H6β), 1.64 (s, 3H, Me19), 1.17 (s, 3H, Me17), 1.12 (s, 3H, Me16), 1.01–0.93 (m, 18H, SiCH₂C$\underline{H}_3$), 0.69–0.52 (m, 12H, SiC$\underline{H}_2$Ch₃), 0.16 (s, 9H, SiC$\underline{H}_3$).

h. 7,10-Bis-O-triethylsilyl-2-debenzoyl-2-(2-furoyl)-10-deacetyl baccatin (III)

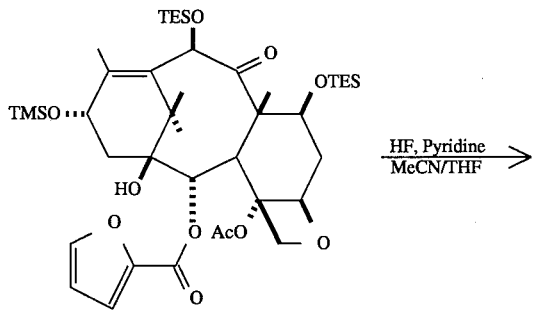

To a solution of 13-O-trimethylsilyl-7,10-bis-O-triethylsilyl-2-debenzoyl-2-(2-furoyl)-10-deacetyl baccatin (III) (30.0 mg, 0.036 mmol) in 2.25 mL of acetonitrile and 2.25 mL of THF in a polyethylene vial was added dropwise 48 μL of pyridine and 75 μL of 48% aqueous HF. The reaction mixture was stirred at 25° C. for 12 h and then diluted with EtOAc (20.0 mL). Saturated aqueous NaHCO₃ was added until gas evolution ceased. The organic layer was separated, washed with brine (3.0 mL), dried over anhydrous Na₂SO₄, filtered and concentrated under reduced pressure to give a crude solid (33.4 mg). Flash chromatography with 30% EtOAc in hexane gave 7,10-bis-O-triethylsilyl-2-debenzoyl-2-(2-furoyl)-10-deacetyl baccatin (HI) (21.3 mg, 78.8% ) and 10-O-triethylsilyl-2-debenzoyl-2-(2-furoyl)-10-deacetyl baccatin (III) (4.9 mg, 21.4%). m.p. 179°–181° C., $[\alpha]^{25}_{Na}$ −45.6° (c 0.5, CHCl₃), ¹H NMR (CDCl₃, 300 MHz) δ7.62 (m, 1H, furoyl), 7.21 (m, 1H, furoyl), 6.53 (m, 1H, furoyl), 5.51 (d, J=7.1 Hz, 1H, H2), 5.20 (s, 1H, H10), 4.94 (dd, J=1.7, 9.3 Hz, 1H, H5), 4.82 (m, 1H, H13), 4.43–4.37 (m, 2H, H7, H20α), 4.18 (d, J=8.2 Hz, 1H, H20β), 3.87 (d, J=7.2 Hz, 1H, H3), 2.52 (m, 1H, H6α), 2.23 (s, 3H, 4Ac), 2.10 (m, 2H, H14α, H14β), 2.01 (s, 3H, Me18), 1.88 (m, 1H, H6β), 1.64(s, 3H, Me19), 1.17 (s, 3H, Me17), 1.04 (s, 3H, Me16), 1.02–0.92 (m, 18H, SiCH₂C$\underline{H}_3$), 0.69–0.54 (m, 12H, SiC$\underline{H}_3$CH₃).

i. 2-Debenzoyl-2-(2-furoyl) taxol.

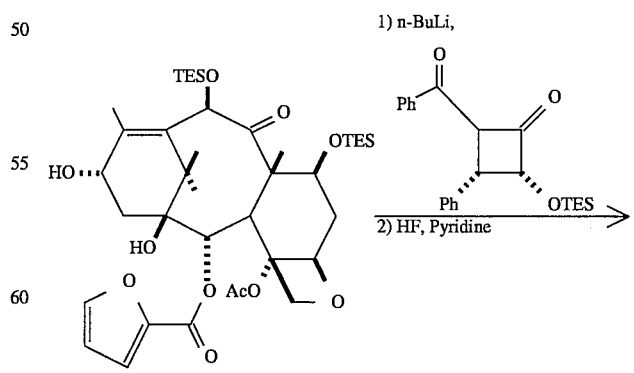

27
-continued

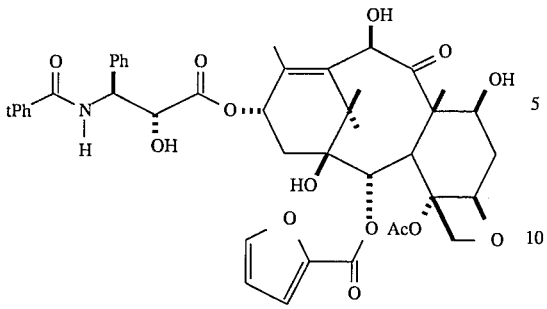

To a solution of 7,10-bis-O-triethylsilyl-2-debenzoyl-2-(2-furoyl)-10-deacetyl baccatin (III) (20 mg, 0.027 mmol) in 1.0 mL of THF at –45° C. was added dropwise 16 μL of a 1.64M solution of n-butyllithium in hexane. After 0.5 h at –45° C., a solution of (±) cis-1-benzoyl-3-triethylsilyloxy-4-phenyl azetidin-2-one (50.0 mg, 0.13 mmol) in THF (0.5 mL) was added dropwise to the mixture. The solution was warmed to 0° C. and kept at that temperature for 1 h and 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel with 20% EtOAc in hexane to give a crude solid (31.7 mg). To a solution of this solid in 1.6 mL of acetonitrile and 79 μL of pyridine at 0° C. was added 240 μL of 48% aqueous HF. The mixture was stirred at 0° C. for 3 h, then at 25° C for 13 h, and, partitioned between saturated aqueous sodium bicarbonate and ethyl acetate. Evaporation of the ethyl acetate solution gave a crude solid (24.4 mg) which was purified by flash chromatography with 70% EtOAc in hexane to give 2-debenzoyl-2-(2-furoyl) taxol (14.9 mg, 68.8%). m.p. 176°–179° C., [α]$^{25}_{Na}$ –43.1° (c 0.5, CHCl₃ ¹H NMR (CDCl₃, 300 MHz) δ7.76–7.32 (m, 12H, aromatic) 7.08 (d, J=8.8 Hz, 1H, NH), 6.60 (m, 1H, furoyl), 6.20 (dd, J=8.8, 8.8 Hz, 1H, H13), 5.78 (dd, J=8.8, 2.8 Hz, 1H, H3'), 5.56 (d, J=7.1 Hz, 1H, H2β), 5.16 (s, 1H, H10), 4.93 (dd, J=9.3, 1.7 Hz, 1H, H5), 4.78 (m, 1H, H2'), 4.40 (d, J=8.3 Hz, 1H, H20α), 4.24 (d, J=8.2 Hz, 1H, 20β), 4.19 (m, 1H, H7), 3.86 (d, J=7.1 Hz, 1H, H3), 3.57 (d, J=5.0 Hz, 1H, 2'OH), 2.56 (m, 1H, H6α), 2.35 (s, 3H, 4Ac), 2.24 (m, 2H, H14α, H14β), 1.83 (m, 1H, H6β), 1.76 (s, 3H, Me18), 1.73 (s, 3H, Me19), 1.19 (s, 3H, Me17), 1.08 (s, 3H, Me16).

EXAMPLE 3

PREPARATION OF TAXOL ANALOGS WITH VARIOUS SUBSTITUENTS AT C-4 a. 13O-Trimethylsilyl-7,10-bis-O-triethylsilyl-2-debenzoyl-4,10-bisdeacetyl
baccatin (III).

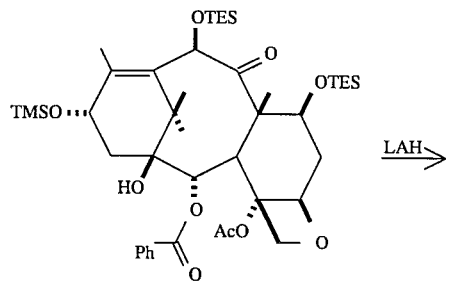

28
-continued

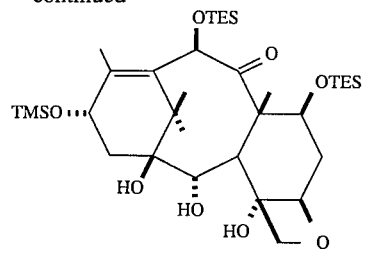

To a solution of 13-O-trimethylsilyl-7,10-bis-O-triethylsilyl-10-deacetyl baccatin (III) (0.1 g, 0.012 mmol) in ether (4.0 mL) at –10° C. was added dropwise 320 μL of a 1.0M solution of lithium aluminum hydride (LAH) in ether. The resulting mixture was slowly warmed from –10° C. to 0° C. over a 2 h period and 3.0 mL of saturated aqueous NaHCO₃ was added. The solution was filtered and the solid was rinsed with EtOAc. The filtrate was concentrated under reduced pressure and diluted with EtOAc (50.0 mL). The organic layer was separated and washed with brine (5.0 mL). The combined organic layer was dried over anhydrous Na₂SO₄, filtered, and concentrated under reduced pressure to give a crude oil (0.15 g). Flash chromatography with 30% EtOAc in hexane gave pure 13-O-trimethylsilyl-7,10-bis-O-triethylsilyl-2-debenzoyl-4,10-bisdeacetyl baccatin (III) (72.0 mg, 85.8%) as a colorless oil. [α]$^{25}$25Na –25.5° (C 0.5, CHCl₃), ¹H NMR (CDCl₃, 300 MHz), δ 5.15 (s, 1H, H10), 4.73 (dd, J=1.8, 8.9 Hz, 1H, H5), 4.65 (m, 1H, H13), 4.53 (d, J=9.3 Hz, 1H, H20α), 4.39 (d, J=8.2 Hz, 1H, H20β), 4.00 (dd, J=6.0, 11.5 Hz, 1H, H7), 3.76 (m, 1H, 2H), 3.44 (d, J=11.0 Hz, 2OH), 3.27 (d, J=6.0 Hz, 1H, H3), 2.45 (m, 2H, H6α, H14α), 2.08–1.93 (m, 2H, H6α, H14β), 1.84 (s, 3H, Me18), 1.53 (s, 3H, Me19), 1.09 (s, 3H, Me17), 1.05 (s, 3H, Me16), 1.01–0.91 (m, 18H, SiCH₂C$\underline{H}$₃), 0.66–0.53 (m, 12H, SiC$\underline{H}$₂CH₃), 0.23 (s, 9H, SiC$\underline{H}$₃).

b. 13-O-Tri methylsilyl-7,10-bis-O-triethylsilyl-2-debenzoyl-10-deacetyl baccatin (III)

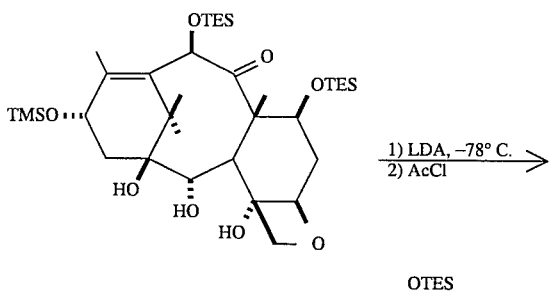

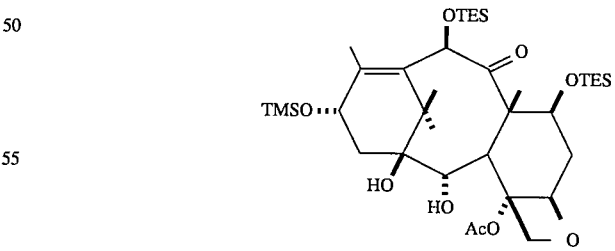

To a solution of 13-O-trimethylsilyl-7,10-bis-O-triethylsilyl-2-debenzoyl-4,10-bisdeacetyl baccatin (III) (10.0 mg, 0.0143 mmol) in THF (1.0 mL) at –78° C. was added 440 μL of a 0.328M solution (10 eq) of lithium diisopropyl amide (LDA) in THF under N₂. The solution was stirred for 30 min at –78° C. and 200 μL of a 1.4M solution of acetyl chloride in THF (20 eq) was added. The mixture were stirred for 1 h at –78° C., saturated aqueous NaHCO₃ (2.0 mL) was added, and the mixture was extracted with EtOAc (2×10 mL). The organic layer was washed with brine (5.0 mL), dried over anhydrous $Na_2SO_4$, filtered and concentrated to give a crude oil (12.7 mg). Flash chromatography from 25% EtOAc to 50% EtOAc in hexane gave 13-O-trimethylsilyl-7,10-bis-O-triethylsilyl-2-debenzoyl-10-deacetyl baccatin (III) (6.1 mg, 57.6%), 13-O-trimethylsilyl-7,10-bis-O-triethylsilyl-2-debenzoyl-2-acetyl-4,10-bisdeacetyl baccatin (III) (1.89 mg, 17.9%), recovered 13-O-trimethylsilyl-7,10-bis-O-triethylsilyl-2-debenzoyl-4,10-bisdeacetyl baccatin (III) (1.2 mg, 12.0%) and 13-O-trimethylsilyl-7,10-bis-O-triethylsilyl-2-debenzoyl-2-acetyl-4,10-bisdeacetyl baccatin (III) (<1.0 mg).

c. 13-O -Trimethylsilyl-7,10-bis-O-triethylsilyl-2-debenzoyl-4,10-bisdeacetyl
   baccatin (III) 1,2-carbonate

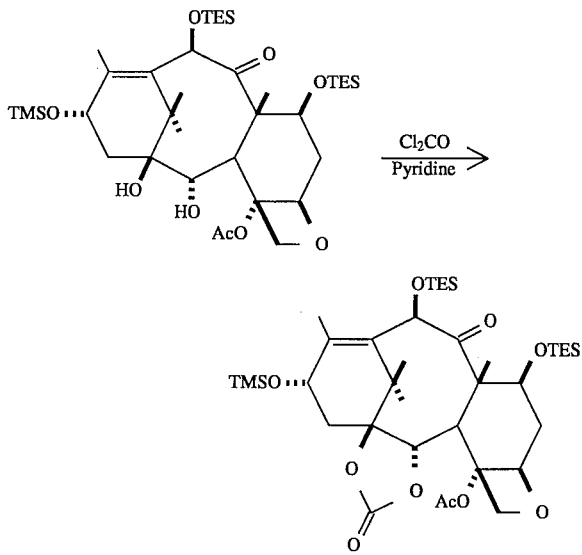

To a solution of 13-O-trimethylsilyl-7,10-bis-O-triethylsilyl-2-debenzoyl-4,10-bisdeacetyl baccatin (III) (20.0 mg, 0.029 mmol) in $CH_2Cl_2$ (4.0 mL) and pyridine (0.8 mL) at −78° C. was added 80 μL of a 3.4M solution of $COCl_2$ in benzene (10 eq). The mixture was warmed to −10° C. (ice-acetone) and kept for 30 min at −10° C. Saturated aqueous $NaHCO_3$ (5.0 mL) was added and the mixture were extracted with EtOAc (3×10 mL). The organic layer was washed with aqueous 10% $CuSO_4$ then brine (5.0 mL), dried over anhydrous $Na_2SO_4$, filtered and concentrated under reduced pressure to give a crude solid (21.9 mg). Plug filtration with 20% EtOAc in hexane gave pure 13-O-trimethylsilyl-7,10-bis-O-triethylsilyl-2-debenzoyl-4,10-bisdeacetyl baccatin (III) 1,2-carbonate (20.8 mg, 98.9%). m.p. 147°–148° C., $[\alpha]^{25}_{Na}$ −28.8° (c 0.5, $CHCl_3$), $^1H$ NMR ($CDCl_3$, 300 MHz), δ5.21 (s, 1H, H10), 4.76 (dd, J=2.8, 9.9 Hz, 1H, H5), 4.65 (m, 1H, H13), 4.54 (d, J=8.8 Hz, 1H, H20α), 4.52 (d, J=8.3 Hz, 1H, H20β), 4.32 (d, J=5.0 Hz, 1H, H2), 4.10 (dd, J=6.6, 11.0 Hz, 1H, H7), 3.10 (d, J=5.3 Hz, 1H, H3), 2.54 (m, 3H, H6α, H14α, H14β), 1.99 (m, 1H, H6β), 1.92 (s, 3H, Me18), 1.61 (s, 3H, Me18), 1.61 (s, 3H, Me19), 1.17 (s, 3H, Me17), 1.12 (s, 3H, Me16), 1.01–0.91 (m, 18H, $SiCH_2CH_3$), 0.67–0.56 (m, 12H, $SiCH_2CH_3$), 0.23 (s, 9H, $SiCH_3$).

d. 13-O-Trimethylsilyl-7,10-bis-O-triethylsilyl-2-debenzoyl-2-acetyl-4,10-bisdeacetyl baccatin (III)

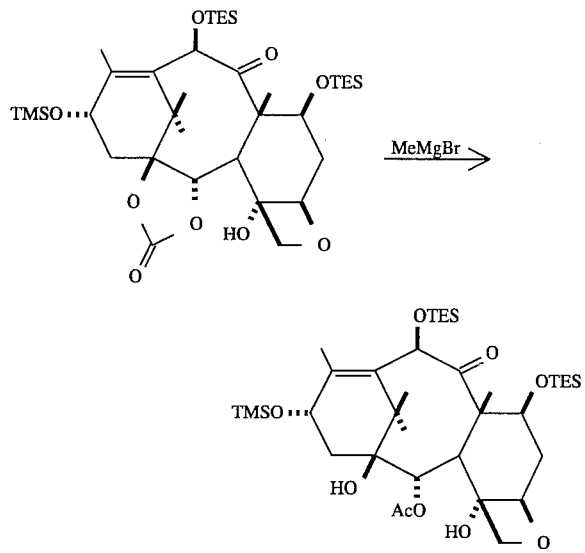

To a solution of 13-O-trimethylsilyl-7,10-bis-O-triethylsilyl-2-debenzoyl-4,10-bisdeacetyl baccatin (III) (10.0 mg, 0.014 mmol) in THF (0.5 mL) at 0° C. was added 40 μL of a 3.4M solution (10 eq) of MeMgBr in ether. The solution was stirred for 1 h at 0° C. under $N_2$ and saturated aqueous $NaHCO_3$ was added (1.0 mL). The mixture was extracted with EtOAc (3×5.0 mL) and the organic layer was washed with brine (5.0 mL), dried over anhydrous $Na_2SO_4$, filtered and concentrated under reduced pressure to give a crude solid (11.9 mg). Flash chromatography with 20% EtOAc in hexane gave pure 13-O-trimethylsilyl-7,10-bis-O-triethylsilyl-2-debenzoyl-2-acetyl-4,10-bisdeacetyl baccatin (III) (9.9 mg, 97.0%). m.p. 198°–201° C., $[\alpha]^{25}_{Na}$ −39.9° (c 0.5, $CHCl_3$), $^1H$ NMR ($CDCl_3$, 300 MHz), δ5.27 (d, J=5.5 Hz, 1H, H2), 5.22 (s, 1H, H10), 4.71 (m, 1H, H13), 4.58 (dd, J=2.8, 9.3 Hz, 1H, H5), 4.41 (d, J=7.7 Hz, 1H, H20α), 4.35 (d, J=7.1 Hz, 1H, H20β), 4.01 (dd, J=6.1, 11.6 Hz, 1H, H7), 3.74 (s, 1H, 4OH), 3.47 (d, J=5.5 Hz, 1H, H3), 2.45 (m, 1H, H6α, 2.24–2.04 (m, 2H, H14α H14β), 2.06 (s, 3H, 2Ac), 1.96 (m, 1H, H6β), 1.88 (s, 3H, Me18), 1.46 (s, 3H, Me18), 1.46 (s, 3H, Me19), 1.14 (s, 3H, Me17), 1.02 (s, 3H, Me16), 0.99–0.91 (m, 18H, $SiCH_2CH_3$), 0.67–0.56 (m, 12H, $SiCH_2CH_3$), 0.24 (s, 9H, $SiCH_3$).

13-O-Trimethylsilyl-7,10-bis-O-triethylsilyl-4,10-bisdeacetyl baccatin (III)

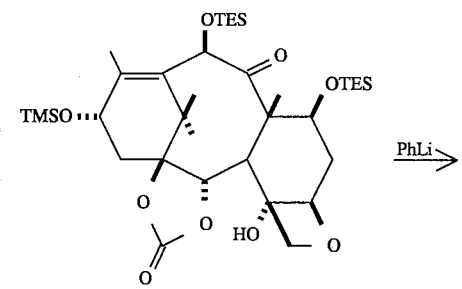

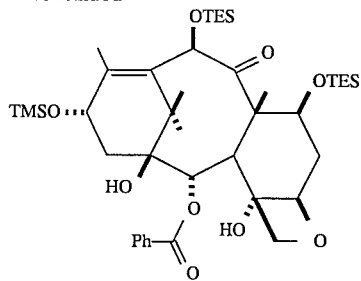

To a solution of 13-O-trimethylsilyl-7,10-bis-O-triethylsilyl-2-debenzoyl-4,10-bisdeacetyl baccatin (III) 1,2-carbonate (10.0 mg, 0.014 mmol) in THF (0.5 mL) at −45° C. was added 78 μL of a 1.8M solution of phenyllithium (10 eq) in 30% ether/70% cyclohexane. The solution was stirred for 1 h at −45° C. under $N_2$ and saturated aqueous NaHCO was added (1.0 mL). The mixture was extracted with EtOAc (3×5.0 mL). The organic layer was washed with brine (5.0 mL), dried over anhydrous $Na_2SO_4$, filtered and concentrated under reduced pressure to give a crude solid (12.8 mg). Flash chromatography with 50% EtOAc in hexane gave pure 13-O-trimethylsilyl-7,10-bis-O-triethylsilyl-4,10-bisdeacetyl baccatin (III) (9.9 mg, 98.5%). m.p. 177°–179° C., $[\alpha]^{25}_{Na}$ −44.5° (c 0.3, $CHCl_3$), $^1H$ NMR ($CDCl_3$, 300 MHz) δ8.05 (d, J=7.2 Hz, 2H, benzoate ortho), 7.60–7.37 (m, 3H, aromatic), 5.61 (d, J=6.1 Hz, 1H, H2), 5.25 (s, 1H, H10), 4.74 (m, 1H, H13), 4.57 (dd, J=1.7, 9.3 Hz, 1H, H5), 4.38 (d, J=8.2 Hz, 1H, H20α), 4.12 (d, J=8.2 Hz, 1H, H20b), 4.05 (dd, J=6.1, 12.1 Hz, 1H, H7), 3.69 (d, J =6.0 Hz, 1H, H3), 2.55 (m, 1H, H6α), 2.42 (m, 2H, H14α, H14β), 2.04 (s, 3H, Me18), 1.99 (m, 1H, H6β), 1.64 (s, 3H, Me19), 1.20 (s, 3H, Me17), 1.04 (s, 3H, Me16), 1.01–0.90 (m, 18H, $SiCH_2CH_3$), 0.70–0.56 (m, 12H, $SiCH_2CH_3$).

f. 13-O-Trimethylsilyl-7,10-bis-O-triethylsilyl-2-debenzoyl-10-deacetyl baccatin (III) 1,2-carbonate

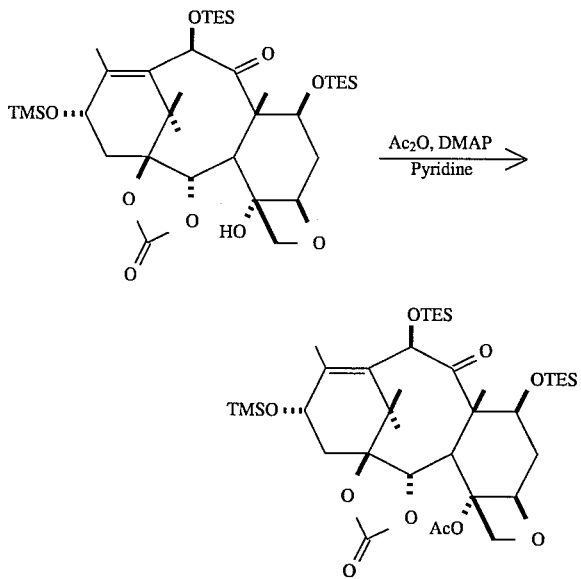

To a stirred solution of 13-O-trimethylsilyl-7,10-bis-Ootriethyl-silyl-2-debenzoyl-4,10-bisdeacetyl baccatin (III) 1,2-carbonate (8.0 mg, 0.011 mmol) in pyridine (0.5 mL) was added $Ac_2O$ (100 μL) and DMAP (50 mg). The solution was heated at reflux under $N_2$ for 12 h, cooled to room temperature, and 15.0 mL of EtOAc was added. The organic layer was washed with 10% aqueous $CuSO_4$ and brine (5.0 mL), dried over anhydrous $Na_2SO_4$, filtered and concentrated under reduced pressure to give a crude solid (22.0 mg). Flash chromatography with 20% EtOAc in hexane gave 13-O-trimethylsilyl-7,10-bis-O-triethylsilyl-2-debenzoyl-10-deacetyl baccatin (III) 1,2-carbonate (4.4 mg, 53.0%) and 13-O-acetyl-7,10-bis-O-triethylsilyl-2-debenzoyl-10-deacetyl baccatin (III) 1,2-carbonate (2.3 mg, 27.8%).

EXAMPLE 4

10-Desacetoxybaccatin III:

To a solution of baccatin III (20 mg; 0.034 mmol) in THF (0.09 mL) at 0° C. under nitrogen was added a solution of $SmI_2$ (0.1M; 0.9 mL; 0.09 mmol) in THF. After stirring 45 minutes at 0° C. the flask was opened to the air, and the reaction mixture diluted with ethyl acetate (10 mL). The mixture was poured into aqueous HCl (0.2N; 25 mL), extracted with ethyl acetate, and the extract was washed successively with saturated aqueous $NaHCO_3$ and brine, dried over $Na_2SO_4$ and evaporated. The product was isolated by flash chromatography ($SiO_2$; 80% ethyl acetate-hexanes) affording 16.6 mg (92%) of 10-desacetoxybaccatin III which was recrystallized from $CHCl_3$-hexanes. mp 230°–232° C. $[\alpha]^{25}_D$=−103.6 (c=0.00195, $CHCl_3$). IR ($cm^{-1}$): 3100, 2970, 2950, 2900, 1750, 1710, 1460, 1370, 1320, 1270, 1255, 1110, 980, 890, 760, 700. $^1$H-nmr (500 MHz, $CDCl_3$) δ8.11 (dd ;2H; J=8.4, 1.2 Hz; o-Bz); 7.61 (dt; 1H; J=7.5,1.2 Hz; p-Bz); 7.48 (brt; 2H; J=7.8 Hz; m-Bz); 5.66 (br d; 1H; J=6.9 Hz; H-2β); 4,98 (br dd; 1H; J=9.4,2; H-5a); 4.83 (br; 1H; w1/2 19 Hz; H-13β); 4.34 (dt; 1H; J=11.2, 7.8Hz; H-7α); 4.31 (br d; 1H; J=8.4 Hz; H-20α); 4.17 (br d; 1H; J=6.9 Hz; H-3α); 4.15 (dd; 1H; J=8.4, 1Hz; H-20β); 3.84 (d; 1H; J=15.6 Hz; H-10α); 3.46 (ddd; 1H; J=15.6,3.7,1.6 Hz; H-10β); 2.64 (ddd; 1H; J=14.4,9.4,6.9 Hz; H-6α); 2.29 (s; 3H; 4-OAc); 2.28 (m; 2H; H-14α and H-14β); 1.95 (t; 3H; J=1.6 Hz; 18-Me); 1.94 (d, 1H; J=6.8 Hz; 13-OH); 1.79 (ddd; 1H; J=14.4, 11.2, 2.1 Hz; H-6β); 1.64 (s; 3H; 19-Me); 1.58 (s; 1H; 1-OH); 1.38 (d; 1H; J=7.8 Hz; 7-OH); 1.13 (s, 3H; 16-Me); 1.06 (s, 3H; 17-Me).

EXAMPLE 5

7-Triethylsilyl-10-desacetoxybaccatin III:

To a stirred solution of 10-desacetoxybaccatin III (10.0 mg; 0.019 mmol) in anhydrous pyridine (0.05 mL) at room temperature and under nitrogen, triethylchlorosilane (15 L; 0.09 mmol) was added and the resulting mixture was stirred at room temperature for 48 h. After diluting with ethyl acetate (5 mL) the mixture was poured into saturated aqueous $NaHCO_3$ (25 mL) and extracted with ethyl acetate. The extract was washed successively with water, 10% aqueous $CuSO_4$ and brine, dried over $Na_2SO_4$ and evaporated. The product was purified by flash chromatography ($SiO_2$; 40% EA-hexanes) affording 11.1 mg (91%) of 7-triethylsilyl-10-desacetoxybaccatin III.

EXAMPLE 6

10-Desacetoxytaxol:

To a stirred solution of taxol (35 mg; 0.041 mmol) in THF (0.1 mL) at 0° C. under nitrogen was added a solution of $SmI_2$ (0.1M; 1.0 mL; 0.10 mmol) in THF. After stirring 45 minutes at 0° C. the flask was opened to the air and the reaction mixture diluted with ethyl acetate (10 mL). The mixture was poured into aqueous HCl (0.2N; 25 mL), extracted with ethyl acetate, and the extract was washed successively with saturated aqueous $NaHCO_3$ and brine, dried over $Na_2SO_4$ and evaporated. The product was isolated by flash chromatography ($SiO_2$; 80% ethyl acetate-hexanes) affording 29.4 mg (90%) of 10-desacetoxytaxol.

What we claimed is:

1. A compound having the formula

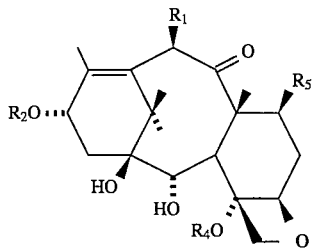

wherein $R_1$ is H, —OH, protected hydroxy, or —$OCOR_6$;

$R_2$ is a hydroxy protecting group;

$R_4$ is H or $R_8CO$—;

$R_5$ is —OH or protected hydroxy; and $R_6$ and $R_8$ are independently H, $C_1$–$C_6$ alkyl, $C_2$–$C_6$ alkenyl, $C_2$–$C_6$ alkynyl, monocyclic aryl, or monocyclic heteroaryl.

2. A compound as set forth in claim 1 wherein $R_4$ is H.

3. A compound having the formula

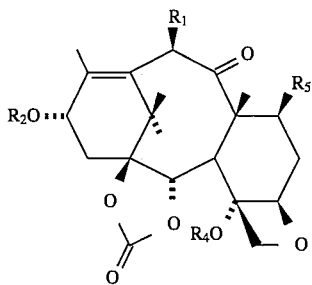

wherein $R_1$ is H, —OH, protected hydroxy, or —$OCOR_6$;

$R_2$ is H or a hydroxy protecting group, or

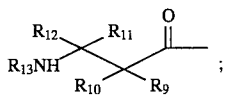

$R_4$ is $R_8CO$—;

$R_5$ is —OH or protected hydroxy;

$R_6$ and $R_8$ are independently H, $C_1$–$C_6$ alkyl, $C_2$–$C_6$ alkenyl, $C_2$–$C_6$ alkynyl, monocyclic aryl, or monocyclic heteroaryl;

$R_9$ is —$OR_{14}$, —$SR_{15}$, or —$NR_{16}R_{17}$;

$R_{10}$ is hydrogen, alkyl, alkenyl, alkynyl, aryl or heteroaryl;

$R_{11}$ and $R_{12}$ are independently hydrogen, alkyl, alkenyl, alkynyl, aryl, acyl or heteroaryl, provided $R_{11}$ and $R_{12}$ are not both acyl;

$R_{13}$ is —$COR_{18}$, —$COOR_{18}$, —$COSR_{18}$, —$CONR_{12}R_{18}$, or —$SO_2R_{19}$;

$R_{14}$ is hydrogen, alkyl, alkenyl, alkynyl, aryl, heteroaryl, or hydroxy protecting group;

$R_{15}$ is alkyl, alkenyl, alkynyl, aryl, heteroaryl, or sulfhydryl protecting group;

$R_{16}$ is hydrogen, alkyl, alkenyl, alkynyl, aryl, or heteroaryl;

$R_{17}$ is an amino protecting group;

$R_{18}$ is alkyl, alkenyl, alkynyl, aryl, or heteroaryl; and $R_{19}$ is alkyl, alkenyl, alkynyl, aryl, heteroaryl, —$OR_{15}$, or —$NR_{12}R_{16}$.

4. A compound of claim 3 wherein $R_2$ is

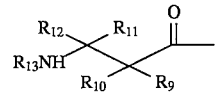

wherein $R_9$ is —$OR_{14}$;

$R_{10}$ is hydrogen;

$R_{11}$ and $R_{12}$ are independently hydrogen, alkyl, alkenyl, alkynyl, aryl, or heteroaryl;

$R_{13}$ is —$COR_{18}$, —$COOR_{18}$, or —$CONR_{12}R_{18}$; and $R_{14}$ is hydrogen or hydroxy protecting group.

5. A compound having the formula

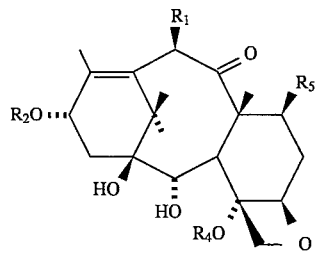

wherein $R_1$ is H, —OH, protected hydroxy, or —$OCOR_6$;

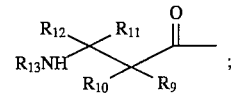

$R_2$ is $R_4$ is H or $R_8CO$—;

$R_5$ is —OH or protected hydroxy;

$R_6$ and $R_8$ are independently H, $C_1$–$C_6$ alkyl, $C_2$–$C_6$ alkenyl, $C_2$–$C_6$ alkynyl, monocyclic aryl, or monocyclic heteroaryl;

$R_9$ is —$OR_{14}$, —$SR_{15}$, or —$NR_{16}R_{17}$;

$R_{10}$ is hydrogen, alkyl, alkenyl, alkynyl, aryl or heteroaryl;

$R_{11}$ and $R_{12}$ are independently hydrogen, alkyl, alkenyl, alkynyl, aryl, acyl or heteroaryl, provided $R_{11}$ and $R_{12}$ are not both acyl;

$R_{13}$ is —$COR_{18}$, —$COOR_{18}$, —$COSR_{18}$, —$CONR_{12}R_{18}$, or —$SO_2R_{19}$;

$R_{14}$ is hydrogen, alkyl, alkenyl, alkynyl, aryl, heteroaryl, or hydroxy protecting group;

$R_{15}$ is alkyl, alkenyl, alkynyl, aryl, heteroaryl, or sulfhydryl protecting group;

$R_{16}$ is hydrogen, alkyl, alkenyl, alkynyl, aryl, or heteroaryl;

$R_{17}$ is an amino protecting group;

$R_{18}$ is alkyl, alkenyl, alkynyl, aryl, or heteroaryl; and $R_{19}$ is alkyl, alkenyl, alkynyl, aryl, heteroaryl, —$OR_{15}$, or —$NR_{12}R_{16}$.

6. A compound of claim 5
wherein
R$_9$ is —OR$_{14}$;
R$_{10}$ is hydrogen;
R$_{11}$ and R$_{12}$ are independently hydrogen, alkyl, alkenyl, alkynyl, aryl, or heteroaryl;
R$_{13}$ is —COR$_{18}$, —COOR$_{18}$, or —CONR$_{12}$R$_{18}$; and
R$_{14}$ is hydrogen or hydroxy protecting group.

7. A compound having the formula

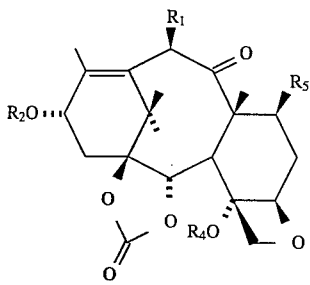

wherein
R$_1$ is H, —OH, protected hydroxy, or —OCOR$_6$;
R$_2$ is H or a hydroxy protecting group, or

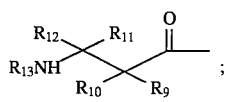

R$_4$ is hydrogen;
R$_5$ is —OH or protected hydroxy;
R$_6$ is H, C$_1$–C$_6$ alkyl, C$_2$–C$_6$ alkenyl, C$_2$–C$_6$ alkynyl, monocyclic aryl, or monocyclic heteroaryl;
R$_9$ is —OR$_{14}$, —SR$_{15}$, or —NR$_{16}$R$_{17}$;
R$_{10}$ is hydrogen, alkyl, alkenyl, alkynyl, aryl or heteroaryl;
R$_{11}$ and R$_{12}$ are independently hydrogen, alkyl, alkenyl, alkynyl, aryl, acyl or heteroaryl, provided R$_{11}$ and R$_{12}$ are not both acyl;
R$_{13}$ is —COR$_{18}$, —COOR$_{18}$, —COSR$_{18}$, —CONR$_{12}$R$_{18}$, or —SO$_2$R$_{19}$;
R$_{14}$ is hydrogen, alkyl, alkenyl, alkynyl, aryl, heteroaryl, or hydroxy protecting group;
R$_{15}$ is alkyl, alkenyl, alkynyl, aryl, heteroaryl, or sulfhydryl protecting group;
R$_{16}$ is hydrogen, alkyl, alkenyl, alkynyl, aryl, or heteroaryl;
R$_{17}$ is an amino protecting group;
R$_{18}$ is alkyl, alkenyl, alkynyl, aryl, or heteroaryl; and
R$_{19}$ is alkyl, alkenyl, alkynyl, aryl, heteroaryl, —OR$_{15}$, or —NR$_{12}$R$_{16}$.

8. A compound of claim 7 wherein R$_2$ is

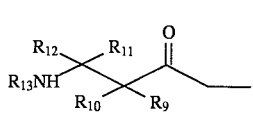

wherein
R$_9$ is —OR$_{14}$;
R$_{10}$ is hydrogen;
R$_{11}$ and R$_{12}$ are independently hydrogen, alkyl, alkenyl, alkynyl, aryl, or heteroaryl;

R$_{13}$ is —COR$_{18}$, —COOR$_{18}$, or —CONR$_{12}$R$_{18}$; and
R$_{14}$ is hydrogen or hydroxy protecting group.

9. A compound of claim 1 wherein R$_1$ is H, —OH, protected hydroxy, or —OCOR$_6$ wherein R$_6$ is C$_1$–C$_6$ alkyl; R$_4$ is H or R$_8$CO—; and R$_8$ is C$_1$–C$_6$ alkyl.

10. A compound of claim 9 wherein R$_1$ is H, —OH, protected hydroxy, or acetoxy, and R$_4$ is H or acetyl.

11. A compound of claim 3 wherein R$_2$ is H or a hydroxy protecting group; R$_1$ is H, —OH, protected hydroxy, or —OCOR$_6$, wherein R$_6$ is C$_1$–C$_6$ alkyl; and R$_8$ is C$_1$–C$_6$ alkyl.

12. A compound of claim 11 wherein R$_1$ is H, —OH, protected hydroxy, or acetoxy and R$_4$ is acetyl.

13. A compound of claim 4 wherein R$_1$ is H, —OH, protected hydroxy, or —OCOR$_6$ wherein R$_6$ is C$_1$–C$_6$ alkyl; and R$_8$ is C$_1$–C$_6$ alkyl.

14. A compound of claim 13 wherein R$_1$ is H, —OH, protected hydroxy, or acetoxy and R$_4$ is acetyl.

15. A compound of claim 4 wherein R$_1$ is H, —OH, protected hydroxy, or —OCOR$_6$ wherein R$_6$ is C$_1$–C$_6$ alkyl; R$_8$ is C$_1$–C$_6$ alkyl; R$_{11}$ is hydrogen; R$_{12}$ is alkyl, alkenyl, aryl, or heteroaryl; R$_{13}$ is —COR$_{18}$ or —COOR$_{18}$; and R$_{18}$ is alkyl, alkenyl, aryl, or heteroaryl.

16. A compound of claim 5 wherein R$_1$ is H, —OH, protected hydroxy, or —OCOR$_6$ wherein R$_6$ is C$_1$–C$_6$ alkyl; and R$_8$ is C$_1$–C$_6$ alkyl.

17. A compound of claim 16 wherein R$_1$ is H, —OH, protected hydroxy, or acetoxy and R$_4$ is acetyl.

18. A compound of claim 6 wherein R$_1$ is H, —OH, protected hydroxy, or —OCOR$_6$ wherein R$_6$ is C$_1$–C$_6$ alkyl; R$_8$ is C$_1$–C$_6$ alkyl; R$_{11}$ is hydrogen; R$_{12}$ is alkyl, alkenyl, aryl, or heteroaryl; R$_{13}$ is —COR$_{18}$ or —COOR$_{18}$; and R$_{18}$ is alkyl, alkenyl, aryl, or heteroaryl.

19. A compound of claim 18 wherein R$_1$ is H, —OH, protected hydroxy, or acetoxy and R$_4$ is acetyl.

20. A compound of claim 7 wherein R$_2$ is H or a hydroxy protecting group; R$_1$ is H, —OH, protected hydroxy, or —OCOR$_6$ wherein R$_6$ is C$_1$–C$_6$ alkyl; and R$_8$ is C$_1$–C$_6$ alkyl.

21. A compound of claim 20 wherein R$_1$ is H, —OH, protected hydroxy, or acetoxy.

22. A compound of claim 8 wherein R$_1$ is H, —OH, protected hydroxy, or —OCOR$_6$ wherein R$_6$ is C$_1$–C$_6$ alkyl.

23. A compound of claim 22 wherein R$_1$ is H, —OH, protected hydroxy, or acetoxy.

24. A compound of claim 8 wherein R$_1$ is H, —OH, protected hydroxy, or —OCOR$_6$ wherein R$_6$ is C$_1$–C$_6$ alkyl; R$_{11}$ is hydrogen; R$_{12}$ is alkyl, alkenyl, aryl, or heteroaryl; R$_{13}$ is —COR$_{18}$ or —COOR$_{18}$; and R$_{18}$ is alkyl, alkenyl, aryl, or heteroaryl.

25. A compound of claim 24 wherein R$_1$ is H, —OH, protected hydroxy, or acetoxy.

26. A compound having the formula

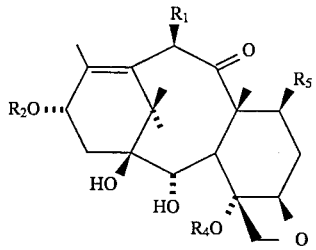

wherein
R$_1$ is H, protected hydroxy, or —OCOR$_6$;
R$_2$ is H;

$R_4$ is H or $R_8CO-$;

$R_5$ is $-OH$ or protected hydroxy; and $R_6$ and $R_8$ are independently H, $C_1-C_6$ alkyl, $C_2-C_6$ alkenyl, $C_2-C_6$ alkynyl, monocyclic aryl, or monocyclic heteroaryl.

27. A compound of claim 26 wherein $R_1$ is H, protected hydroxy, or $-OCOR_6$ wherein $R_6$ is $C_1-C_6$ alkyl; $R_4$ is H or $R_8CO-$; and $R_8$ is $C_1-C_6$ alkyl.

28. A compound of claim 27 wherein $R_1$ is H, protected hydroxy, or acetoxy, and $R_4$ is H or acetyl.

29. A compound having the formula

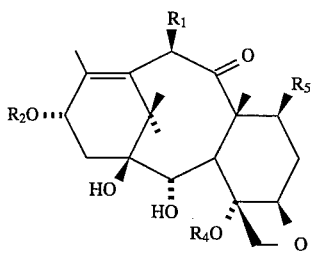

wherein $R_1$ is H, $-OH$, protected hydroxy, or $-OCOR_6$;

$R_2$ is H;

$R_4$ is H or $R_8CO-$;

$R_5$ is $-OH$; and $R_6$ and $R_8$ are independently H, $C_1-C_6$ alkyl, $C_2-C_6$ alkenyl, $C_2-C_6$ alkynyl, monocyclic aryl, or monocyclic heteroaryl.

30. A compound of claim 29 wherein $R_1$ is H, $-OH$, protected hydroxy, or $-OCOR_6$ wherein $R_6$ is $C_1-C_6$ alkyl; $R_4$ is H or $R_8CO-$; and $R_8$ is $C_1-C$alkyl.

31. A compound of claim 30 wherein $R_1$ is H, $-OH$, protected hydroxy, or acetoxy, and $R_4$ is H or acetyl.

32. A compound having the formula

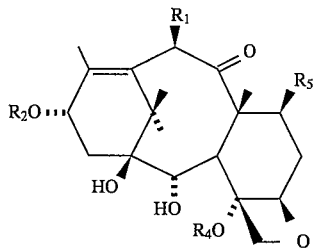

wherein $R_1$ is H, $-OH$, protected hydroxy, or $-OCOR_6$;

$R_2$ is H;

$R_4$ is $R_8CO-$;

$R_5$ is $-OH$ or protected hydroxy; and $R_6$ and $R_8$ are independently H, $C_1-C_6$ alkyl, $C_2-C_6$ alkenyl, $C_2-C_6$ alkynyl, monocyclic aryl, or monocyclic heteroaryl.

33. A compound of claim 32 wherein $R_1$ is H, $-OH$, protected hydroxy, or $-OCOR_6$ wherein $R_6$ is $C_1-C_6$ alkyl; $R_4$ is $R_8CO-$; and $R_8$ is $C_1-C_6$ alkyl.

34. A compound of claim 33 wherein $R_1$ is H, $-OH$, protected hydroxy, or acetoxy, and $R_4$ is acetyl.

* * * * *

UNITED STATES PATENT AND TRADEMARK OFFICE
CERTIFICATE OF CORRECTION

PATENT NO.    : 5,587,489
DATED         : December 24, 1996
INVENTOR(S)   : Robert A. Holton and Seokchan Kim It is certified that error appears in the above-identified patent and that said Letters Patent is hereby corrected as shown below:

Column 1,
Line 7, "NIH Grant #CA 55131" should read -- NIH Grant #CA 42031 and #CA 55131 --.

Column 4,
Line 31, " "AR" " should read -- "Ar" --.

Columns 7 and 8,
In "-continued Scheme 1" the third recited structure should read:
--

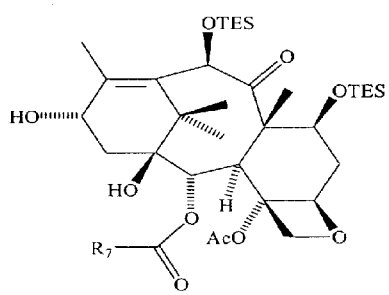

--

Columns 13 and 14,
Scheme 6 should read:
--

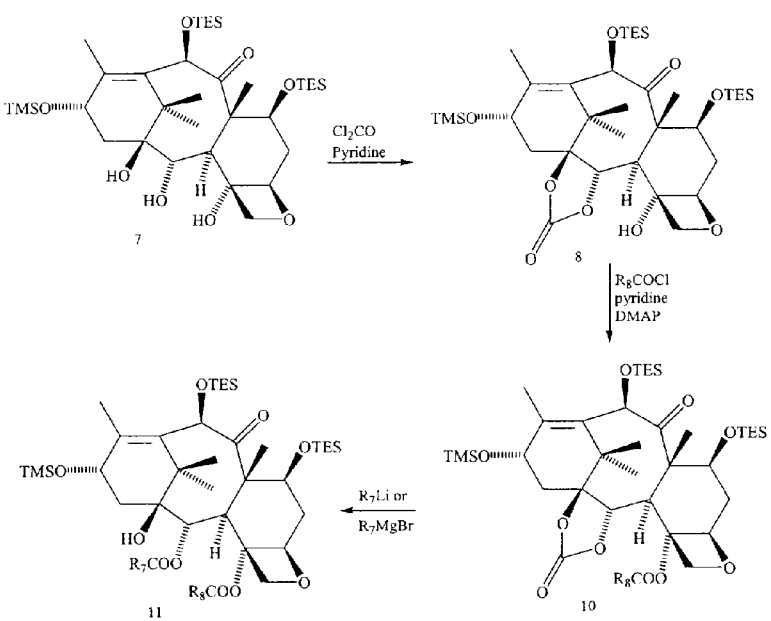

UNITED STATES PATENT AND TRADEMARK OFFICE
CERTIFICATE OF CORRECTION

PATENT NO.  : 5,587,489
DATED       : December 24, 1996
INVENTOR(S) : Robert A. Holton and Seokchan Kim It is certified that error appears in the above-identified patent and that said Letters Patent is hereby corrected as shown below:

Column 18,
Line 24, that portion of the structure reading "imidazole, DMAP" should read
-- Imidazole, DMAP --.

Column 21,
Line 25, "-10deacetyl" should read -- -10-deacetyl --.
Line 65, that portion reading "13-0-" should read -- c. 13-0- --.

Column 23,
Line 22, "7,10-Bis-" should read -- e. 7,10-Bis- --.

Column 24,
Line 5, before the chemical structures, insert -- f. 2-Debenzoyl-2-p-fluorobenzoyl taxol --.

Column 26,
Line 47, "SiCH$_3$CH$_3$)." should read -- SiCH$_2$CH$_3$). --.

Column 27,
Line 52, that portion reading "130-Trimethylsilyl-" should read
-- 13-0-Trimethylsilyl- --.

Column 30,
Line 53, that portion reading "13-0-" should read -- e. 13-0- --.

Column 34,
Line 20, "is hydrogen" should read -- R$_{14}$ is hydrogen --.
Lines 36-42, should read:
-- R$_2$ is

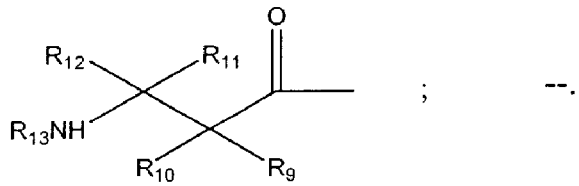

;       --.

UNITED STATES PATENT AND TRADEMARK OFFICE
CERTIFICATE OF CORRECTION

PATENT NO. : 5,587,489
DATED : December 24, 1996
INVENTOR(S) : Robert A. Holton and Seokchan Kim It is certified that error appears in the above-identified patent and that said Letters Patent is hereby corrected as shown below:

Column 37,
Line 35, "$C_1$-Calkyl." should read -- $C_1$-$C_6$ alkyl. --.

Signed and Sealed this

Twenty-fourth Day of September, 2002

Attest:

JAMES E. ROGAN
Attesting Officer   Director of the United States Patent and Trademark Office